(12) United States Patent
Hamdan et al.

(10) Patent No.: US 12,209,139 B2
(45) Date of Patent: Jan. 28, 2025

(54) N- AND C-TERMINAL TANDEM TAG SYSTEM FOR PURIFICATION

(71) Applicant: King Abdullah University of Science and Technology, Thuwal (SA)

(72) Inventors: Samir M. Hamdan, Thuwal (SA); Vlad-Stefan Raducanu, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

(21) Appl. No.: 17/408,328

(22) Filed: Aug. 20, 2021

(65) Prior Publication Data

US 2022/0056072 A1    Feb. 24, 2022

Related U.S. Application Data

(60) Provisional application No. 63/068,163, filed on Aug. 20, 2020.

(51) Int. Cl.
| | |
|---|---|
| C07K 1/22 | (2006.01) |
| C07K 2/00 | (2006.01) |
| C07K 14/195 | (2006.01) |
| C12N 9/48 | (2006.01) |
| C12N 15/62 | (2006.01) |
| C12N 15/70 | (2006.01) |
| C12P 21/00 | (2006.01) |

(52) U.S. Cl.
CPC .............. *C07K 2/00* (2013.01); *C12N 15/62* (2013.01); *C12N 15/70* (2013.01); *C07K 2319/21* (2013.01); *C07K 2319/22* (2013.01); *C07K 2319/23* (2013.01); *C07K 2319/24* (2013.01); *C07K 2319/41* (2013.01); *C07K 2319/42* (2013.01); *C07K 2319/43* (2013.01); *C07K 2319/50* (2013.01)

(58) Field of Classification Search
CPC .......... C07K 14/195; C07K 1/22; C12N 9/00; C12N 9/48; C12P 21/00
See application file for complete search history.

(56) References Cited

U.S. PATENT DOCUMENTS

| | | | |
|---|---|---|---|
| 8,945,876 B2 * | 2/2015 | Su ...................... | C12N 15/8201 435/69.7 |
| 2013/0131315 A1 * | 5/2013 | Su ......................... | C12P 21/00 536/23.1 |
| 2019/0276501 A1 * | 9/2019 | Yung ................ | C07K 14/43563 |

OTHER PUBLICATIONS

Bajar, et al., "Improving brightness and photostability of green and red fluorescent proteins for live cell imaging and FRET reporting", Sci. Rep., 6:20889 (2016).
Barondeau, et al., "Understanding GFP posttranslational chemistry: structures of designed 5 variants that achieve backbone fragmentation, hydrolysis, and decarboxylation", J. Am. Chem. Soc., 128(14):4685-93 (2006).
Bernard, et al., "Tight attachment of chitin binding-domain-tagged proteins to surfaces coated with acetylated chitosan", Anal. Biochem., 327(2):278-83 (2004).
Block, et al., "Immobilized-metal affinity chromatography (IMAC): a review", Methods Enzymol., 463:439-73 (2009).
Bornhorst, et al., "Purification of proteins using polyhistidine affinity tags", Methods Enzymol., 326:245-54 (2000).
Boshart, et al., "A Very Strong Enhancer Is Located Upstream of an Immediate Early Gene of Human Cytomegalovirus", Cell, 41:521-530 (1985).
Braakman, et al., "Manipulating disulfide bond formation and protein folding in the endoplasmic reticulum", EMBO J., 11(5):1717-22 (1992).
Costa, et al., "Fusion tags for protein solubility, purification and immunogenicity in *Escherichia coli*: the novel Fh8 system", Front. Microbiol., 5:63 (2014).
Evans, et al., "Semisynthesis of cytotoxic proteins using a modified protein splicing element", Protein Sci., 7(11):2256-64 (1998).
Fischer, et al., "Comparative assessment of different histidine-tags for immobilization of protein onto surface plasmon resonance sensorchips", Anal. Chem., 83(5):1800-7 (2011).
Frey, et al., "A new set of highly efficient, tag-cleaving proteases for purifying recombinant proteins", J. Chromatogr. A, 1337:95-105 (2014).
Gonzales, et al., "Bacterial aminopeptidases: properties and functions", FEMS Microbiol. Rev., 18(4):319-44 (1996).
Gorman, et al., "Protein disulfide bond determination by mass spectrometry", Mass Spectrom Rev., 21(3):183-216 (2002).
Goulatis, et al., "Impacts of the −1 Amino Acid on Yeast Production of Protein-Intein Fusions", Biotechnol. Prog., 35(1):e2736 (2019)., et al., "Impacts of the −1 Amino Acid on Yeast Production of Protein-Intein Fusions", Biotechnol. Prog., 35(1): e2736 (2019).
Gradia, et al., "MacroBac: New Technologies for Robust and Efficient Large-Scale Production of Recombinant Multiprotein Complexes", Methods Enzymol., 592:1-26 (2017).
Ivanov, et al., "One-step purification of twin-strep-tagged proteins and their complexes on strep-tactin resin cross-linked with bis-(sulfosuccinimidyl) suberate (BS3)", J. Vis. Exp. (86): 51536 (2014).
Jankiewicz, et al., "The properties and functions of bacterial aminopeptidases", Acta Microbiol. Pol., 52(3):217-31 (2003).

(Continued)

*Primary Examiner* — Maryam Monshipouri
(74) *Attorney, Agent, or Firm* — PABST PATENT GROUP LLP

(57) ABSTRACT

Expression vectors and methods of protein purification, which allow for selection of full length protein over truncated forms of the protein being purified, are disclosed. The methods express a target protein as a three domain fusion, represented by formula I: A-[Li]-B-[L2]-C, where A is a first purification tag domain, C is the second purification tag domain and B is the target protein domain. A, B and C are preferably covalently linked by linkers, $L_1$ and $L_2$ may be optional. The purification tags at the N and C termini are different. The purification tags at the N and C termini are different. Expression vectors including nucleic acid sequences which encode the fusion protein represented by formula I are also disclosed. The vectors are used with host expression systems such as insect, yeast, or mammalian cells to express the target protein, which is subsequently purified as a function of the different affinity tags.

13 Claims, 20 Drawing Sheets

Specification includes a Sequence Listing.

(56) References Cited

OTHER PUBLICATIONS

Jennings, et al., "Elimination of truncated recombinant protein expressed in *Escherichia coli* by removing cryptic 5 translation initiation site", Protein Expr. Purif., 121:17-21 (2016).
Kaufman, et al., "Construction of a modular dihydrofolate reductase cDNA gene: analysis of signals utilized for efficient expression", Mol. Cell. Biol, 2(11):1304-1319 (1982).
Khan, et al., "Double-hexahistidine tag with high-affinity binding for protein immobilization, purification, and detection on ni30 nitrilotriacetic acid surfaces", Anal. Chem., 78(9):3072-9 (2006).
Kimple, et al., "Overview of affinity tags for protein purification", Curr. Protoc. Protein Sci., 73:9.9.1-9.9.23 (2013).
Lavallie, et al., "Thioredoxin as a fusion partner for production of soluble recombinant proteins in *Escherichia coli*.", Methods Enzymol., 326:322-40 (2000).
Leavesley, et al., "Assessing FRET using spectral techniques", Cytometry A, 83(10):898-912 (2013).
Lykkemark, et al., "Degradation of C terminal tag sequences on domain antibodies purified from *E. coli* supernatant", MAbs, 6(6): 1551-9 (2014).
Miller, et al., "Peptidases and proteases of *Escherichia coli* and *Salmonella typhimurium*", Annu. Rev. Microbiol., 29:485-504 (1975).
Mitchell, et al., "Protein Affinity Purification using Intein/ ChitinBinding Protein Tags", Methods Enzymol., 559:111-25(2015).
Mormann, et al., "Fragmentation of intra-peptide and inter-peptide disulfide bonds of proteolytic peptides by nanoESI collision-induced dissociation", Anal. Bioanal. Chem., 392(5):831-8 (2008).
Narayanan, et al., "Alleviation of proteolytic sensitivity to enhance recombinant lipase production in *Escherichia coli*.", Appl. Environ. Microbiol., 75(16):5424-7 (2009).
Palmiter, et al., "Metallothionein-Human GH Fusion Genes Stimulate Growth of Mice", Science, 222(4625):809-814 (1983).
Panavas, et al., "SUMO fusion technology for enhanced protein production in prokaryotic and eukaryotic expression systems", Methods Mol. Biol., 497:303-17 (2009).
Parsell, et al., "Carboxy-terminal determinants of intracellular protein degradation", Genes Dev., 4(2):277-86 (1990).
Qian, et al., "Fluorescence resonance energy transfer detection methods: Sensitized emission and acceptor bleaching", Exp. Ther. Med., 30 8(5):1375-1380 (2014).
Raducanu, et al., "Two chromatographic schemes for protein purification involving the biotin/avidin interaction under native conditions", J. Chromatogr. A., 1621:461051 (2020).
Raran-Kurussi, et al., "Removal of Affinity Tags with TEV Protease", Methods Mol. Biol., 1586:221-230 (2017).
Rosano, et al., "Recombinant protein expression in *Escherichia coli*: advances and challenges", Front. Microbiol., 5:172 (2014).
Ryan, et al., "Overview of approaches to preventing and avoiding proteolysis during expression and purification of proteins", Curr. Protoc. Protein Sci., Chapter 5:Unit5 25 (2013).
Schmidt, et al., "Development of the Twin-Strep-tag(R) and its application for purification of recombinant proteins from cell culture supernatants", Protein Expr. Purif., 92(1):54-61 (2013).
Southworth, et al., "Purification of proteins fused to either the amino or carboxy terminus of the Mycobacterium xenopi gyrase A intein", Biotechniques, 27(1):110-16, 118-20 (1999).
Spriestersbach, et al. "Chapter One-Purification of His-Tagged Proteins", Methods Enzymol., 559:1-15 (2015).
Subramani, et al., "Expression of the mouse dihydrofolate reductase complementary deoxyribonucleic acid in simian virus 40 vectors", Mol. Cell. Biol., 1(9):854-864 (1981).
Tehseen, et al., "Proliferating cell nuclear antigen-agarose col. A tag-free and tag-dependent tool for protein purification affinity chromatography", J. Chromatogr. A, 1602:341-349 (2019).
Terpe, "Overview of tag protein fusions: from molecular and biochemical fundamentals to commercial systems", Appl. Microbiol. Biotechnol., 60(5):523-33 (2003).
Waugh, "An overview of enzymatic reagents for the removal of affinity tags", Protein Expr. Purif., 80(2):283-93 (2011).
Whitaker, et al., "Avoidance of truncated proteins from unintended ribosome binding sites within heterologous protein coding sequences", ACS Synth. Biol., 4(3):249-57 (2015).
Wingfield, "Overview of the purification of recombinant proteins", Curr. Protoc. Protein Sci., 80:6.1.1-6.1.35 (2015).
Xie, et al., "Effects of thioredoxin: SUMO and intein on soluble fusion expression of an antimicrobial peptide OG2 in *Escherichia coli*.", Protein Pept. Lett., 20(1):54-60 (2013).
Xu, et al., "Purification of recombinant proteins from *E. coli* by engineered inteins", Methods Mol. Biol., 205:43-68 (2003).
Xu, et al., "Fusions to self-splicing inteins for protein purification", Methods Enzymol. 326:376-418 (2000).
Young, et al., "Recombinant protein expression and purification: a comprehensive review of affinity tags and microbial applications", Biotechnol. J., 7(5):620-34 (2012).

\* cited by examiner

N- AND C-TERMINAL TANDEM TAG SYSTEM FOR PURIFICATION

CROSS-REFERENCE TO RELATED APPLICATIONS

This application claims benefit of U.S. Provisional Application No. 62/068,163, filed on Aug. 20, 2020, which is hereby incorporated herein by reference in its entirety.

REFERENCE TO SEQUENCE LISTING

The Sequence Listing submitted Nov. 8, 2021 as a text file named "KAUST_123-02_ST25.txt," created on Nov. 2, 2021, and having a size of 17,402 bytes is hereby incorporated by reference.

FIELD OF THE INVENTION

This invention is generally in the field of protein purification.

BACKGROUND OF THE INVENTION

The use of composite tags fused to a protein of interest to improve protein expression, solubility and purification has gained increasing popularity in protein science[1-4]. Despite their advantages, fusion tags can introduce a various number of undesired amino acids to the N-terminus and/or to the C-terminus in the protein of interest. To solve this problem, cleavable fusion tags have been developed[5,6]. The nature of these cleavable tags, however, usually limits their usability to either the N- or the C-terminus. Moreover, even after successful cleavage, a vast majority of these tags, for example the ones derived from the TEV technology[7], result in undesired remaining amino acids that may interfere with protein function. Additionally, many protein purification methods do not allow for selected of full length protein over truncated forms and degraded protein forms[8], which have caused long-standing problems in protein purification.

Thus there is a need for improved methods of protein purification, which allow for selection of full length protein over truncated forms.

SUMMARY OF THE INVENTION

Expression vectors and methods of protein purification, which allow for selection of full length protein over truncated forms of the protein being purified, are disclosed. The protein to be purified is expressed as a recombinant fusion protein, which includes an N terminal and a C terminal purification tag. The fusion protein is expressed as a three domain fusion, represented by formula I:

A-[L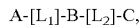]-B-[L$_2$]-C, where A is a first purification tag domain, C is the second purification tag domain and B is the target protein domain. A, B and C are preferably covalently linked by linkers, $L_1$ and $L_2$ as shown in Formula I, however, $L_1$ and $L_2$ may be optional.

A method for purifying a target protein by providing a vector encoding a recombinant fusion protein represented by formula I:

A-[L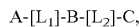]-B-[L$_2$]-C, where A is a first purification tag domain, C is the second purification tag domain and B is the target protein domain. A, B and C are preferably covalently linked by linkers, $L_1$ and $L_2$ as shown in Formula I, however, $L_1$ and $L_2$ may be optional.

Each purification tag domain includes a purification tag, a solubilization tag and a cleavage tag, which themselves are optionally separated by linkers.

Purification tag domains A and C in one preferred embodiment each include an affinity tag, preferably, different affinity tags i.e., the affinity tag in A is different from the affinity tag in C, and in a preferred embodiment, at least double affinity tags, which are each preferably separated by linkers.

Expression vectors including nucleic acid sequences which encode the fusion protein represented by formula I are also disclosed. The vectors are used in connection with host expression systems such as insect, yeast, or mammalian cells to express the target protein, which is subsequently purified as a function of the affinity tags in the purification domain. A preferred expression system is a bacterial expression system, such as E. coli.

BRIEF DESCRIPTION OF THE DRAWINGS

FIG. 2A shows the amino acid sequence (SEQ ID NO:1) of empty TSGIT and RNA sequence (SEQ ID NO:2) encoding it. The amino acid sequence and the corresponding nucleotide sequence are presented in FASTA format. The different tags that compose TSGIT are identified by their corresponding color code. The sequence encoding the protein of interest is cloned into pTSGIT by Gibson Assembly cloning between the SUMO and Intein regions. FIG. 2B top panel shows the amino acid sequence (SEQ ID NO: 3) of the mRuby3 insert. The amino acids sequence and the corresponding nucleotide sequence (SEQ ID NO:4) are presented in FASTA format. The initial methionine is absent as it is not required by the TSGIT fusion expression system. This sequence was cloned into pTSGIT by Gibson Assembly cloning between the SUMO and Intein regions; middle panel: Amino acid sequence of the gp2.5 insert. The amino acids sequence (SEQ ID NO:-22) and the corresponding nucleotide sequence (SEQ ID NO:-23) are presented in FASTA format. The initial methionine is absent as it is not required by the TSGIT fusion expression system. This sequence was assembled together with the TSGIT N- and C-terminal fusion tags between the SUMO-tag and Intein-tag regions by Gibson assembly into a pRSF-1b plasmid.; bottom panel is a schematic representation of the cascade of chemical reactions that leads to the cleavage of the C-terminal fusion tag via traceless Intein cleavage at its N-terminal junction; based on the reaction schemes presented in30,61.

FIG. 3A is a schematic of the procedure employed for purification of mRuby3 using TSGIT. FIG. 3B is an image of an SDS-PAGE gel showing the different steps of purification of mRuby3 starting from E. coli lysate containing the expression product of the pTSGIT-mRuby3 expression vector: lane 1, soluble fraction of the lysate; lane 2, flow-through of the first HisTrap affinity column; lane 3, TSGIT-mRuby3 elution from the HisTrap affinity column; lane 4, flow-through of the first StrepTrap affinity column; lane 5, elution of TSGIT-mRuby3 from StrepTrap affinity column; lane 6, release of mRuby3 from the TSGIT-mRuby3 fusion via SUMO protease and 2-MESNA cleavage; lane 7, flow-through of cleaved mRuby3 through the second HisTrap affinity column; lane 8, flow-through of cleaved mRuby3 through the second StrepTrap affinity column; lane 9, mRuby3 after Superdex 75 pg size-exclusion elution. The marker (M) is PageRuler Prestained Protein Ladder. FIG. 3C is a schematic representation of the IPL reaction of activated mRuby3 produced by TSGIT and the biotin-containing BioP peptide. FIG. 3D is a bar chart illustrating the percentage of flow-through, wash and bound fractions of unlabeled and IPL biotin-labeled mRuby3 from NeutrAvidin resin. The inset schematic shows the three coexisting populations: unlabeled mRuby3, free and NeutrAvidin-bound biotin-labeled mRuby3. FIG. 3E is an image of an SDS-PAGE gel showing the sample (S), flow-through (F), wash (W) and bound (B) fractions of unlabeled and IPL biotin-labeled mRuby3 from NeutrAvidin resin. The marker (M) is the 40 kDa band of PageRuler Prestained Protein Ladder.

FIG. 4A. Emission spectra of various concentrations of NeutrAvidin$^{DyLight650}$. Corrected and normalized emission spectra of various concentrations of NeutrAvidin$^{DyLight650}$ in the presence of (FIG. 4B) 50 nM unlabeled mRuby3 or (FIG. 4C) 50 nM IPL biotin-labeled mRuby3. All data points represent the average of three independent acquisitions. All spectra were collected between 530 and 750 nm upon excitation at 520 nm. All spectra follow the color codes presented in the inset tables. Correction and normalization of the emission spectra were performed as described in the Materials and Methods section. (FIG. 4D) Plot of the enhancement in corrected and normalized emission intensity at 673 nm upon addition of various concentrations of NeutrAvidin$^{DyLight650}$ to 50 nM unlabeled mRuby3 (blue crosses) or to 50 nM IPL biotin-labeled mRuby3 (red circles). All error bars represent the standard deviation of three independent acquisitions. For IPL biotin-labeled mRuby3, the experimental datapoints were fit to a Hill equation. The parameters of the fit are described in the inset table together with their standard deviations. The 95% confidence bounds of the fitted model are depicted by the dashed lines. In all panels, the concentration of NeutrAvidin$^{DyLight650}$ is indicated as the concentration of NeutrAvidin monomers, i.e., biotin binding sites.

FIG. 5A is an image of a 10% SDS-PAGE gel showing the different steps of purification of gp2.5 starting from E. colily sate containing the expression product of the pTSGIT-gp2.5 expression vector: Lane 1, soluble fraction of the lysate; Lane 2, flow-through of the first HisTrap affinity column; Lane 3, TSGIT-gp2.5 elution from the HisTrap affinity column; Lane 4, flow-through of the first StrepTrap affinity column; Lane 5, elution of TSGIT-gp2.5 from StrepTrap affinity column; Lane 6, release of gp2.5 from the TSGIT-gp2.5 fusion via SUMO protease and DTT cleavage; Lane 7, flow-through of cleaved gp2.5 through the second HisTrap affinity column; Lane 8, flow-through of cleaved gp2.5 through the second StrepTrap affinity column; Lane 9, gp2.5 after Superdex 75 pg size-exclusion elution. The marker (M) is PageRuler Prestained Protein Ladder. FIG. 5B includes chromatograms showing the elution of TSGIT-purified gp2.5 (top) and four different molecular weight markers (bottom) from the Superdex 75 pg size-exclusion column. FIG. 5C is an image of a 12% SDS-PAGE gel showing a better separation of the proteins in the gray dashed area from the 10% SDS-PAGE shown in panel (a) with the same numbering of the lanes. FIG. 5D is a schematic representation of the PIFE assay used to monitor the binding affinity of gp2.5 to short ssDNA. FIG. 5E shows examples of time-resolved fluorescence decays of the Cy3-labelled ssDNA obtained in the presence of various concentrations of TSGIT-purified gp2.5.

FIG. 6A is a schematic representation of the single-molecule flow-stretching bead assay used to monitor the elongation of collapsed long ssDNA upon binding of gp2.5. The position of the DNA-attached bead is monitored over time and converted to dsDNA extension equivalent length as described in Materials and Methods section. FIG. 6B is an example of a single-molecule time-trace showing the stretching of the ssDNA-containing substrate upon injection of native tag-free purified gp2.5. FIG. 6C is an example of a single-molecule time-trace showing the stretching of the ssDNA-containing substrate upon injection of TSGIT-purified gp2.5. For both panels, the maximum extension was calculated between the initial and final basslines along the y-axis. FIG. 6D is a plot of the empirical cumulative distribution function, obtained from the indicated number (N) of individual time-traces, of the maximum dsDNA equivalent stretching length by native tag-free-purified gp2.5 (blue) and TSGIT-purified gp2.5 (red). The average stretching length together with its standard deviation is indicated for both proteins.

(FIG. 7A) A plot of the proportion of resin pores available to the molecule (Kay) versus the logarithm with base 10 of the relative molecular weight of the four molecular weight markers (green) obtained from the size-calibration of the Superdex 75 pg column shown in the bottom panel of FIG. 5b. The experimental datapoints were fitted with a linear dependence characterized by an intercept of 2.3702 and a slope of −0.4642. Using the position of the maximum of the elution peak of TSGIT-purified from the same size exclusion column (top panel in FIG. 5b), the size of the protein was estimated (red) from the linear fit by inverting the linear dependence equation. (FIG. 7B) Top: a chromatogram showing the elution of TSGIT-gp2.5 fusion (with both the N- and C-terminal fusion tags uncleaved, as obtained after the first Strep elution step; Lane 5 in FIG. 5a) from the Superdex 200 pg size-exclusion column. Bottom: a chromatogram showing the elution of four different molecular weight markers from the Superdex 200 pg size-exclusion column. The position of the peaks (green dashed lines) were determined as described above. (FIG. 7C) A plot of the proportion of resin pores available to the molecule (Kay) versus the logarithm with base 10 of the relative molecular weight of the four molecular weight markers (green) obtained from the size-calibration of the Superdex 200 pg column shown in the bottom panel of FIG. S5b. The experimental datapoints were fitted with a linear dependence characterized by an intercept of 2.1567 and a slope of −0.3613. Using the position of the maximum of the elution peak of TSGIT-gp2.5 uncleaved fusion from the same size exclusion column (top panel in FIG. S5b), the size of the protein was estimated (red) from the linear fit by inverting the linear dependence equation. (FIG. 7D) Examples of time-resolved fluorescence decays of the Cy3-labelled ssDNA obtained in the presence of various concentrations of native tag-free-purified gp2.5. The curves respect the color code presented in the inset legend.

(FIG. 8A) Additional example of a single-molecule time-trace showing the stretching of the ssDNA-containing substrate upon injection of native tag-free-purified gp2.5. (FIG. 8B) Additional example of a single-molecule time-trace showing the stretching of the ssDNA-containing substrate upon injection of TSGIT-purified gp2.5.

DETAILED DESCRIPTION OF THE INVENTION

Figure 1A:
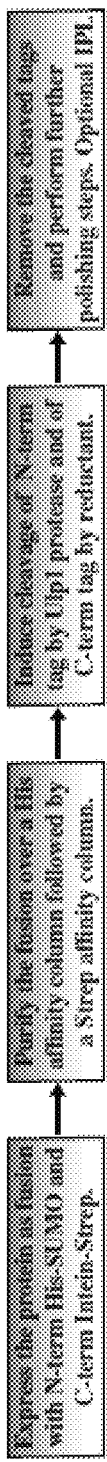
FIG. 1A is a schematic showing the Workflow diagram for protein expression and purification using TSGIT.

A large variety of fusion tags have been developed to improve protein expression, solubilization and purification. Nevertheless, these tags have been combined in a rather limited number of composite tags and usually these composite tags have been dictated by traditional commercially-available expression vectors. Moreover, most commercially-available expression vectors include either N- or C-terminal fusion tags but not both.

A method of protein purification and associated tags are disclosed which allow protein purification to select full length protein over truncated forms and degraded protein forms[8], which have caused long-standing problems in protein purification. Three main mechanisms can generate these unwanted truncated protein forms. First, they can be generated directly during protein expression and in some cases the truncated form remains soluble and consequently can be carried on to the purification step[9-11]. Second, proteolytic cleavage can occur at various positions inside the protein's backbone during expression or even during purification[12-14]. Third, depending on the protein's structure and its amino acid sequence, sequential degradation of the N-terminus[14-16] or C-terminus[14,17,18] can occur. Depending on the amount of similarity between the full-length protein and its truncated forms, the truncated forms may or may not be removed during purification[8-11].

To overcome these aforementioned limitations, a system that employs two different composite tags at the N- and C-termini, each containing a different affinity tag has been developed. Sequential selection for the N- and then the C-terminal affinity tags would therefore select for the full-length protein over its truncated versions. Moreover, these affinity tags were combined with cleavable tags to allow for their removal. The disclosed methods use TSGIT, a fusion-tag system composed of both N- and a C-terminal composite fusion tags. The system preferably includes at least two affinity tags, two solubilization tags and two cleavage tags distributed at both termini of the protein of interest. Therefore, the N- and the C-terminal composite fusion tags in TSGIT are fully orthogonal in terms of both affinity selection and cleavage. For using TSGIT, the cloning, expression and purification procedures is streamlined. Each component tag is selected to maximize its benefits towards the final construct. By expressing and partially purifying the protein of interest between the components of the TSGIT fusion, the full-length protein is selected over truncated forms, which has been a long-standing problem in protein purification. Moreover, due to the nature of the cleavage tags in TSGIT, the protein of interest is obtained in its native form without any additional undesired N- or C-terminal amino acids. Finally, the resulting purified protein is ready for efficient ligation with other proteins or peptides for downstream applications. The use of this system by describing its ability to purify a large amount of native fluorescent mRuby3 protein.

I. Definitions

"Affinity interactions" as used herein refers to the combination of non-covalent interactions between a ligand and its binding partner to form a complex.

"Affinity tags" are defined herein as molecular species which form highly specific, non-covalent, physiochemical interactions with defined binding partners. Affinity tags which form highly specific, non-covalent, physiochemical interactions with one another are defined herein as "complementary".

"Covalent linkage", refers to a bond or organic moiety that covalently links molecules (e.g. fusion proteins) to a non-cellular surface.

The term "target protein" refers to the protein that is to be expressed.

As used herein, "transformed" and "transfected" encompass the introduction of a nucleic acid (e.g. a vector) into a cell by a number of techniques known in the art.

As used herein, a "vector" is a replicon, such as a plasmid, phage, or cosmid, into which another DNA segment may be inserted so as to bring about the replication of the inserted segment. The vectors described herein can be expression vectors.

As used herein, an "expression vector" is a vector that includes one or more expression control sequences. An "expression control sequence" is a DNA sequence that controls and regulates the transcription and/or translation of another DNA sequence.

II. Compositions

Figure 1B:
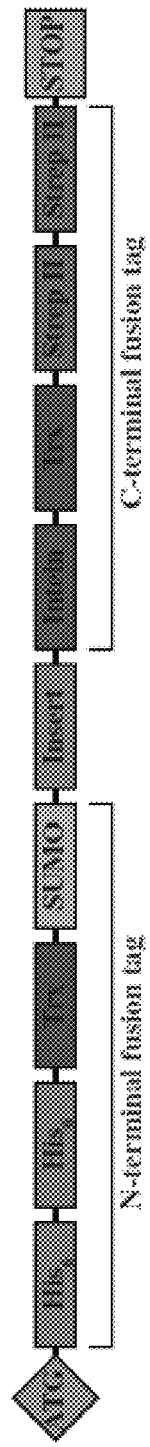
FIG. 1B is a schematic representation of component tags of the TSGIT fusion system.

Fusion proteins where two different affinity tags are placed at the N- and C-termini of the protein of interest are disclosed herein, as well as expression constructs for expressing the fusion protein (for its subsequent purification). The fusion protein includes three domains, represented by formula I:

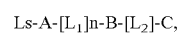

Where A is a first purification tag domain, C is the second purification tag domain and B is the protein domain. A, B and C may be covalently linked by linkers, $L_1$ and $L_2$ as shown in Formula I i.e., $L_1$ and $L_2$ are optional Ls is an optional linker such as GSE (FIG. 2). A schematic representation of this preferred fusion protein is shown in FIG. 1B.

The protein domain includes the amino acid sequence of the protein of interest. Purification tag domain A and B each include a purification tag, preferably an affinity tag, a cleavage tag, and in some preferred embodiments, a solubilization tag which themselves are optionally separated by linkers represented by Formula II.

Where P is the purification tag, n is an integer ranging from 1-6, $L_a$ is an optional linker, S is a solubilization tag, $L_b$ is an optional linker, and $L_1/L_2$ are optional linkers as shown in Formula I and D is a cleavage tag preferably a protease cleavage domain. Preferred cleavage tags are SUMO (small ubiquitin-like modifier, Smt3p) and Intein[29-33] (optimized Mxe GyrA intein). FIG. 2 shows an exemplary amino acid sequence and the corresponding nucleotide sequence, presented in FASTA format. The different tags that compose TSGIT are identified by their corresponding color code. The sequence encoding the protein of interest is cloned into pTSGIT by Gibson Assembly cloning between the SUMO and Intein regions.

A fusion protein as disclosed therein is preferably represented by formula III:

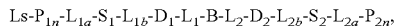

where:

$P_{1n}$ is a first purification tag with n occurrences, where n is an integer as previously defined, ranging from 1-6;
$S_1$ is a first solubilization tag,
$L_{1a}$ is a first optional linker which is a linker between the first solubilization tag and the first purification tag;
$D_1$ is a first cleavage tag, preferably a protease cleavage tag;
$L_{1b}$ is a first optional linker which is a linker between the first solubilization tag and the first cleavage tag;
B is the target protein sequence;
$L_1$ is an optional linker between the first cleavage tag and the target protein sequence;
$D_2$ is a second cleavage tag, preferably a protease cleavage tag;
$L_2$ is an optional linker between the second cleavage tag and the target protein sequence;
$S_2$ is a second solubilization tag,
$L_{2b}$ is a second optional linker which is a linker between the second solubilization tag and the second cleavage tag;
$P_{2n}$ is a second purification tag with "n" occurrences, where n is an integer as previously defined, ranging from 1-6; and
$L_{2a}$ is a second optional linker which is a linker between the second solubilization tag and the second purification tag.

Purification tag domains A and C in one preferred embodiment each include an affinity tag, i.e., $P_1$ and $P_2$ are affinity tags, preferably, different affinity tags i.e., the affinity tag in A is different from the affinity tag in C i.e., $P_1$ is different from $P_2$. In a preferred embodiment, purification tag domains A and C include at least double affinity tags, which are each preferably separated by linkers, i.e., $P_1$-$L$-$P_1$ and $P_2$-$L$-$P_2$. Referring to Formula III, $P_1$ or $P_2$ is preferably H6 or Strep II. See FIG. 1B. Thus, in one embodiment, when $P_1$ is H6, L is GGSS (SEQ ID NO: 7), $P_2$ is a strep tag, L is GGGSGGGSGGS (SEQ ID NO:21)

Referring to Formula III:
Ls-$P_{1n}$-$L_{1a}$-$S_1$-$L_{1b}$-$D_1$-$L_1$-B-$L_2$-$D_2$-$L_{2b}$-$S_2$-$L_{2a}$-$P_{2n}$, in a particularly preferred embodiment, Ls is preferably GSE; For $P_{1n}$, $P_i$ is preferably H6 and n is 2; -$L_{1a}$ is preferably GGSS (SEQ ID NO:7); $S_1$ is TRX; $L_{1b}$ is GGSS (SEQ ID NO:7; $D_1$ is SUMO; $L_1$ is present or optional; B is the target protein being purified; $L_2$ is present or optional; $D_2$ is intein; $L_{2b}$ is TGLTGLNSGL (SEQ ID NO: 8); $S_2$ is TRX; $L_{2a}$ is GGSS (SEQ ID NO:7); and for $P_{2n}$, $P_2$ is a strep tag and n is 2 (FIG. 2).

A. Purification Tags

The disclosed fusion proteins are preferably purified by reliance on non-covalent interactions for purification. The fusion protein is expressed as a recombinant fusion protein which includes component that binds to an affinity binding partner. In some preferred embodiments the affinity purification system utilizing non-covalent linkage includes one or more linkers, for example, one or more glycine-serine linkers.

A preferred non-covalent linkage is provided by the affinity interactions involved receptor-ligand complex formation. Binding of a ligand to its binding partner can occur by intermolecular forces, such as ionic bonds, hydrogen bonds, hydrophobic interactions and Van der Waals forces. Thus, affinity interactions as used herein refers to the combination of non-covalent interactions between a ligand and its binding partner to form a complex.

Exemplary affinity tags include the polyhistidine affinity tag, also known as the His-tag or $His_6$, usually consists of six consecutive histidine residues, but can vary in length from two to ten histidine residues; FLAG tags, which typically include the sequence DYKDDDDK (SEQ ID NO:16); haemagglutinin (HA) for example, YPYDVP (SEQ ID NO:17); MYC tag for example ILKKATAYIL (SEQ ID NO:18) or EQKLISEEDL (SEQ ID NO:20); Strep-tag WSHPQFEK (SEQ ID NO: 19), glutathione S-transferase (GST); Maltose binding protein (MBP), calmodulin binding peptide (CBP); the intein-chitin binding domain (intein-CBD), the streptavidin tag, etc. Methods of using purification tags to facilitate protein purification are known in the art and include, for example, a chromatography step wherein the tag reversibly binds to a chromatography resin.

Purifications tags are introduced in the N-terminal and C-terminal to the fusion protein. Protein purification tags such as affinity tags are known in the art (reviewed in Kimple, et al., *Curr Protoc Protein Sci*. 2013; 73: Unit-9.9)

Histidine readily forms coordination bonds with immobilized transition metal ions. Immobilized $Co^{2+}$, $cu^{2+}$, $Ni^{2+}$, $Zn^{2+}$, $Ca^{2+}$, and $Fe^{3+}$ can all be used to purify polyhistidine fusion proteins, but $Ni^{2+}$ is the most commonly used. If purification by $Ni^{2+}$ is unsatisfactory, empirical determination of the most effective transition metal ion for purification of a specific polyhistidine fusion protein can be performed. There are several companies that offer IMAC resin. The matrix most widely used for IMAC is Ni(II)-nitrilotriacetic acid (Ni-NTA), available from Qiagen. Other resins used for the immobilization of transition metal ions include iminodiacetic acid agarose (chelating Sepharose, GE Healthcare) and carboxymethylaspartate agarose (Talon resin, Clontech). A His tagged fusion protein can then be purified from its medium (e.g. cell lysate) using suitable purification systems, such as an affinity column (e.g. a HisTrap™ affinity column). HisTrap™ HP is a ready to use column, prepacked with precharged Ni Sepharose™ High Performance which has high binding capacity and low nickel ion leakage that ensures reliable capture of target protein. Ni Sepharose High Performance (HP) affinity resists consists of highly cross-linked agarose beads to which a chelating group has been coupled. This chelating group is precharged with nickel, which selectively retains proteins with exposed histidine groups.

The pGEX E. coli expression vectors, which encode for N-terminal glutathione S-transferase (GST) molecules followed by protease cleavage sites, available from GE Healthcare in all three reading frames and with three different protease cleavage sites (e.g., thrombin, factor Xa, and PreScission). GST fusion proteins can be purified by affinity chromatography (UNIT 6.6) on commercially available glutathione (γ-glutamylcysteinylglycine) Sepharose ($K_d$=0.6 nM), which is affected by γ-glutamyl transpeptidase activity in crude cell lysates. Glutathione affinity chromatography is amenable to low concentrations of denaturing agents (2 to 3 M urea or guanidine hydrochloride), reducing agents (<10 mM 2-mercaptoethanol or dithiothreitol), and nonionic detergents (2% v/v Tween 20), depending on the nature of the fusion protein. GST fusion proteins are incubated with glutathione Sepharose in order to facilitate crosslinking between the two. The elution with 10 mM glutathione is relatively mild, often preserving protein function and antigenicity. A 70 kDa E. coli heat-shock-induced chaperonin often copurifies with eluted GST fusion proteins. This contaminant can be removed by treatment of cell lysates with 5 mM $MgCl_2$ and 5 mM ATP prior to purification. Furthermore, GST can be cleaved from its fusion protein while still bound to glutathione agarose, providing a convenient method for separating the 26 kDa GST from the protein of interest.

Maltose binding protein (MBP) is often used to increase the expression level and/or solubility of its fusion partner, with typical yields of 10 to 40 mg fusion protein per liter culture. pMAL vectors are available for cytoplasmic or periplasmic expression in all three reading frames, with factor Xa, enterokinase, or genenase I protease cleavage sequences (New England Biolabs). Other MBP fusion vectors include pIVEX (Roche), which can be used for coupled in vitro transcription/translation. MBP fusion proteins can be purified by affinity chromatography on cross-linked amylose resin. Amylose resins are commercially available but are affected by amylase activity in crude cell lysates.

The calmodulin binding peptide (CBP) purification system utilizes a C-terminal fragment from muscle myosin light-chain kinase in order to purify proteins of interest from bacteria. With low levels of calcium present at physiological pH, this 26 amino acid fragment displays a fairly strong affinity ($K_d$=$10^{-9}$M) for the protein calmodulin. Removal of calcium causes calmodulin to undergo a conformational change resulting in the release of its ligand. T7-based pET expression vectors have been engineered to allow attachment of the CBP affinity tag to either the C- or N-terminal of the fusion protein.

The intein-chitin binding domain (intein-CBD) tag is a combination of a protein self-splicing element (intein) with a chitin-binding domain and allows for the purification of a native recombinant protein without need for a protease. The intein self-cleavage reaction is induced by overnight incubation with 50 mM DTT at 4° C. 2-mercaptoethanol, cysteine, or hydroxylamine may also be used but are less effective.

B. Solubilization Tags

In some embodiments, the compositions disclosed herein include expression or solubility enhancing amino acid sequence, hereinafter, solubilization tags. The expression or solubility enhancing amino acid sequence can be cleaved in the recombinant expression system, or after the expressed protein in purified. Solubilization tags are used, especially for recombinant proteins expressed in chaperone-deficient species such as E. coli, to assist in the proper folding in proteins and keep them from precipitating. Commercially available vectors provide for intein-CBD expression on the N-terminus, C-terminus, or both termini of a heterologous protein of interest (IMPACT system, New England Biolabs).

Exemplary sequences include thioredoxin (TRX) and poly(NANP). Some affinity tags have a dual role as a solubilization agent, such as MBP (maltose binding protein), and GST (glutathione-s-transferase), C. Cleavage Tags The cleavage tag preferably is small ubiquitin-related modifier (SUMO) or Intein ((optimized Mxe GyrA intein) FIG. 2).

SUMO is a member of a ubiquitin-like protein superfamily that is covalently attached to target proteins as a post-translational modification to alter the localization, stability, and/or function of the target protein in response to changes in the cellular environment.

D. Linkers

Linkers included in the disclosed fusion protein are preferably flexible linkers. Preferably the peptide or polypeptide domains are flexible peptides or polypeptides. A "flexible linker" herein refers to a linker such as a peptide or polypeptide containing two or more amino acid residues joined by peptide bond(s) that provides increased rotational freedom for two polypeptides linked thereby than the two linked polypeptides would have in the absence of the flexible linker. Preferred linkers are flexible linkers such as glycine-serine, (GGGGS)n (SEQ ID NO:14), for example, GGGGS (SEQ ID NO: 5), GGGS (SEQ ID NO: 6), GGSS (SEQ ID NO:7), Thr-Gly-Leu-Thr-Gly-Leu-Asn-Ser-Gly-Leu (SEQ ID NO:8) and GSE (SEQ ID NO:9). Other exemplary flexible peptides/polypeptides that can be included in the disclosed fusion proteins include, but are not limited to, the amino acid sequences Gly-Ser, Gly-Ser-Gly-Ser (SEQ ID NO:10), Ala-Ser, $(Gly_4\text{-}Ser)_3$ (SEQ ID NO:11), and $(Gly_4\text{-}Ser)_4$ (SEQ ID NO:12), GSGSGSGS (SEQ ID NO:13). Additional flexible peptide/polypeptide sequences are well known in the art. In one embodiment, $L_1$ is SGSG (SEQ ID NO:15).

In one preferred embodiment for the N-terminal purification tag, a double His6-tag (two consecutive hexa-histidine tags connected by a glycine2-serine2 flexible linker) is selected as the purification tag, Trx (Thioredoxin) as the solubilization tag and SUMO (small ubiquitin-like modifier, Smt3p) as the cleavage tag. His-tag-capturing media exhibits high dynamic binding capacity and therefore can capture large amounts of the protein of interest, whereas the SUMO-tag is efficiently cleaved via Ulp1 SUMO protease without leaving any additional N-terminal amino acids.

In one preferred embodiment for the C-terminal purification tag, a Twin Strep-tag (two consecutive Strep-tag IIs connected by an optimized flexible linker) is selected as the purification tag for example, the sequence AWSHPQFEKGGGSGGGSGGSAWSHPQFEK (SEQ ID NO:24) (FIG. 2)), Trx as the solubilization tag and Intein (optimized Mxe GyrA intein) as the cleavage tag. The Twin Strep-tag exhibits high specificity and results in sharp chromatographic peaks, which makes its elution ideal for subsequent purification steps. The Intein-tag is efficiently cleaved by reducing agents without leaving any additional C-terminal amino acids. Moreover, SUMO and Intein cleavage can proceed simultaneously for optimizing the duration of the protocol. In addition, the use of the Intein-tag allows the target protein to be ready for intein-mediated protein ligation (IPL). The use of this preferred system, referred to herein as TSGIT for Trx-SUMO-Gene of interest-Intein-Trx, by expressing and purifying native mRuby3 fluorescent protein. The examples below demonstrate most preferred embodiments showing streamlined TSGIT's cloning, expression and purification protocols for maximum ease of use and time efficiency.

II. Method of Protein Purification

Fusion proteins of Formula I can be obtained by, for example, by chemical synthesis, and more preferably, by recombinant production in a host cell. To recombinantly produce a fusion proteins of Formula I, a nucleic acid containing a nucleotide sequence encoding the polypeptide can be used to transform, transduce, or transfect a bacterial or eukaryotic host cell (e.g., an insect, yeast, or mammalian cell). In general, nucleic acid constructs include a regulatory sequence operably linked to a nucleotide sequence encoding a fusion proteins of Formula I.

The method includes: (a) expressing a target protein as a fusion protein including at least two purification tags each at the C and N terminal ends of the protein using a suitable protein expression system, where a preferred purification tag is an affinity tag; (b) purifying the fusion protein sequency using a system containing a binding partner for the first affinity tag, followed by a binding partner for the second affinity tag; (c) cleave the N and C terminal tags using proteases that recognize the cleavage tags in the purification domains of the fusion protein and (d) removing the cleaved tags. (FIG. 1A).

The fusion protein is engineered to include three domains, represented by Formula I:

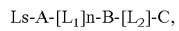

Where A is a first purification tag domain, C is the second purification tag domain and B is the protein domain. A, B and C may be covalently linked by linkers, $L_1$ and $L_2$ as shown in Formula I. i.e., $L_1$ and $L_2$ are be optional Ls is an optional linker such as GSE (FIG. 2). A schematic representation of this preferred fusion protein is shown in FIG. 1B. The protein domain includes the amino acid sequence of the protein of interest. Purification tag domain A and B each include a purification tag, preferably an affinity tag, a cleavage tag, and in some preferred embodiments, a solubilization tag which themselves are optionally separated by linkers represented by Formula II.

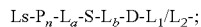

Where P is the purification tag, n is an integer ranging from 1-6, $L_a$ is an optional linker, S is a solubilization tag, $L_b$ is an optional linker, and $L_1/L_2$ are optional linkers as shown in Formula I and D is a cleavage tag preferably a protease cleavage domain. Preferred cleavage tags are SUMO (small ubiquitin-like modifier, Smt3p) and Intein[29-33] (optimized Mxe GyrA intein). FIG. 2 shows an exemplary amino acid sequence and the corresponding nucleotide sequence, presented in FASTA format. The different tags that compose TSGIT are identified by their corresponding color code. The sequence encoding the protein of interest is cloned into pTSGIT by Gibson Assembly cloning between the SUMO and Intein regions.

An expression vector is engineered to express a fusion protein as disclosed herein is preferably represented by Formula III: Ls-$P_{1n}$-$L_{1a}$-$S_1$-$L_{1b}$-$D_1$-$L_1$-B-$L_2$-$D_2$-$L_{2b}$-$S_2$-$L_{2a}$-$P_{2n}$, where: $P_{1n}$ is a first purification tag with n occurrences, where n is an integer as previously defined, ranging from 1-6; $S_1$ is a first solubilization tag, $L_{1a}$ is a first optional linker which is a linker between the first solubilization tag and the first purification tag; $D_1$ is a first cleavage tag, preferably a protease cleavage tag; $L_{1b}$ is a first optional linker which is a linker between the first solubilization tag and the first cleavage tag;

B is the target protein sequence;

$L_1$ is an optional linker between the first cleavage tag and the target protein sequence;

$D_2$ is a second cleavage tag, preferably a protease cleavage tag;

$L_2$ is an optional linker between the second cleavage tag and the target protein sequence;

$S_2$ is a second solubilization tag, $L_{2b}$ is a second optional linker which is a linker between the second solubilization tag and the second cleavage tag;

$P_{2n}$ is a second purification tag with "n" occurrences, where n is an integer as previously defined, ranging from 1-6; and $L_{2a}$ is a second optional linker which is a linker between the second solubilization tag and the second purification tag.

The expression vector encodes fusion proteins with purification tag domains A and C in one preferred embodiment each including an affinity tag, i.e., $P_1$ and $P_2$ are affinity tags, preferably, different affinity tags i.e., the affinity tag in A is different from the affinity tag in C i.e., $P_1$ is different from $P_2$. In a preferred embodiment, purification tag domains A and C include at least double affinity tags, which are each preferably separated by linkers, i.e., $P_1$-L-$P_1$ and $P_2$-L-$P_2$ Referring to Formula III, $P_1$ or $P_2$ is preferably H6 or Strep II. See FIG. 1B. Thus, in one embodiment, when $P_1$ is H6, L is GGSS (SEQ ID NO: 7), $P_2$ is a strep tag, L is GGGSGGGSGGS (SEQ ID NO:21).

Referring to Formula III:

Ls-$P_{1n}$-$L_{1a}$-$S_1$-$L_{1b}$-$D_1$-$L_1$-B-$L_2$-$D_2$-$L_{2b}$-$S_2$-$L_{2a}$-$P_{2n}$, in a particularly preferred embodiment, Ls is preferably GSE; For $P_{1n}$, $P_1$ is preferably H6 and n is 2; -$L_{1a}$ is preferably GGSS (SEQ ID NO:7); $S_1$ is TRX; $L_{1b}$ is GGSS (SEQ ID NO:7); $D_1$ is SUMO; $L_1$ is present or optional; B is the target protein being purified; $L_2$ is present or optional; $D_2$ is intein; $L_{2b}$ is TGLTGLNSGL (SEQ ID NO: 8); $S_2$ is TRX; $L_{2a}$ is GGSS (SEQ ID NO:7); and for $P_{2n}$, $P_2$ is a strep tag and n is 2 (FIG. 2).

Nucleic acid sequences which encode the disclosed peptide domains required by the disclosed fusion proteins are known in the art.

Useful prokaryotic and eukaryotic systems for expressing and producing polypeptides are well known in the art include, for example, *Escherichia coli* strains such as BL-21, and cultured mammalian cells such as CHO cells. Preferably, the genetic sequence is introduced into the organism via a vector.

In eukaryotic host cells, a number of viral-based expression systems can be utilized to express fusion proteins of Formula I. Viral based expression systems are well known in the art and include, but are not limited to, baculoviral, SV40, retroviral, or vaccinia based viral vectors.

Methods of making and using vectors for in vivo insertion of nucleic acids are known in the art.

The disclosed construct (expression vectors) are used to address a long-standing problem related to the presence of truncated protein forms in a complex mixture sample. In many cases, these truncated forms are hardly separable from the desired full-length protein. The full-length protein is selected by sequential chromatographic steps based on the affinity tags attached to the fusion protein. The tags are cleaved in solution by two different mechanisms and the final protein is free of any undesired additional amino acids.

Expression Vector

The disclosed expression vectors are designed based on a fusion design where two different affinity tags in purification domains (as described above) are placed at the N- and C-termini of the protein of interest. A preferred expression vector is designed as exemplified in the materials and methods.

The expression vector is made by employing conventional molecular biology, microbiology and recombinant DNA techniques that are known in the art. These techniques are well known and fully disclosed in the literature. See for example Sambrook and Russel (Eds). Molecular cloning, A Laboratory Manual, 2001, Cold Spring Harbor Labs, Cold Spring Harbor Press, NY; Oligonucleotide Synthesis, M J Gait, Ed., 1984; Transcription and Translation, Hames & Higgins, 1984.

Expression vectors for use in expressing the fusion protein will comprise a promoter capable of directing the transcription of a cloned gene or cDNA. The promoter may be any DNA sequence, which shows transcriptional activity in the host cell of choice and may be derived from genes encoding proteins either homologous or heterologous to the host cell. Expression vectors for use in expressing the fusion protein will comprise a promoter capable of directing the transcription of a cloned gene or cDNA. The promoter may be any DNA sequence, which shows transcriptional activity in the host cell of choice and may be derived from genes encoding proteins either homologous or heterologous to the host cell. Examples of suitable promoters for directing the transcription of the DNA in mammalian cells are the SV40 promoter (Subramani et al., Mol. Cell. Biol. 1 (1981), 854-864), the MT-1 (metallothionein gene) promoter (Palmiter et al., Science 222 (1983), 809-814), the CMV promoter (Boshart et al., Cell 41:521-530, 1985) or the adenovirus 2 major late promoter (Kaufman and Sharp, Mol. Cell. Biol, 2:1304-1319, 1982).

The nucleotide sequences encoding the fusion protein are usually inserted into a recombinant vector which may be any vector, which may conveniently be subjected to recombinant DNA procedures, and the choice of vector will often depend on the host cell into which it is to be introduced. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated. The vector is preferably an expression vector in which the DNA sequence encoding the fusion protein is operably linked to additional segments required for transcription of the DNA. In general, the expression vector is derived from plasmid or viral DNA or may contain elements of both. The term, "operably linked" indicates that the segments are arranged so that they function in concert for their intended purposes, e.g. transcription initiates in a promoter and proceeds through the DNA sequence coding for the fusion protein.

Suitable expression vectors include, without limitation, plasmids and viral vectors derived from, for example, bacteriophage, baculoviruses, tobacco mosaic virus, herpes viruses, cytomegalo virus, retroviruses, vaccinia viruses, adenoviruses, lentiviruses and adeno-associated viruses. Numerous vectors and expression systems are commercially available from such corporations as Novagen (Madison, Wis.), Clontech (Palo Alto, Calif.), Stratagene (La Jolla, Calif.), and Invitrogen Life Technologies (Carlsbad, Calif.).

Regulatory Sequences

Regulatory sequences (also referred to herein as expression control sequences) typically do not encode a gene product, but instead affect the expression of the nucleic acid sequences to which they are operably linked.

Nucleic acids in vectors can be operably linked to one or more expression control sequences. For example, the control sequence can be incorporated into a genetic construct so that expression control sequences effectively control expression of a coding sequence of interest. Examples of expression control sequences include promoters, enhancers, and transcription terminating regions.

A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Protein Recovery

The expressed tagged or fusion proteins produced by the cells may be recovered from the culture medium by conventional procedures including separating the host cells from the medium by centrifugation or filtration, releasing the fusion protein by mechanical cell disruption, such as ultrasonication or pressure, precipitating the protein aqueous components of the supernatant or filtrate by means of a salt, e.g. ammonium sulphate.

The soluble portion fraction of cell lysates is subjected to purification using a binding partner for a first affinity tag in the fusion protein, the bound proteins are eluted and then brought in contact with a binding partner for the second affinity tag in the fusion protein.

In some preferred forms, fusion protein is captured from lysate through its His tag. So IMAC (immobilized metal affinity chromatography) is used and then, after concentration of protein-containing fractions, they are subjected to size exclusion chromatography (SEC) for final purification.

It is to be understood that the disclosed method and compositions are not limited to specific synthetic methods, specific analytical techniques, or to particular reagents unless otherwise specified, and, as such, can vary. It is also to be understood that the terminology used herein is for the purpose of describing particular embodiments only and is not intended to be limiting.

Any discussion of documents, acts, materials, devices, articles or the like which has been included in the present specification is not to be taken as an admission that any or all these matters form part of the prior art base or were common general knowledge in the field relevant to the present disclosure as it existed before the priority date of each claim of this application.

The disclosed compositions and methods can be further understood through the following examples.

EXAMPLES

Materials and Methods

Plasmid Design and Construction

For the component tags of the TSGIT fusion, their amino acid sequences were selected from well-established available sources. For the N-terminal part of the fusion, the two His-tags consist of six consecutive histidine residues[43,44] and the SUMO-tag sequence was chosen from the pE-SUMO expression vector (LifeSensors). For the C-terminal part of the fusion, the Intein-tag sequence and its subsequent linker were chosen from the pTXB1 expression vector (IMAPC system, New England BioLabs) and the sequence of the Twin Strep-tag was selected as the one described previosuly[27,28]. The Trx-tag sequence used for both parts of the fusion was selected from the 2T-T expression vector (MacroBac system[45]). All these amino acid sequences were converted to coding DNA sequences by the codon optimization tool available on-line from Integrated DNA Technologies (IDT).

The genes encoding the empty full-length TSGIT construct (FIG. 2), its N-terminal part only or its C-terminal part only were custom synthesized by IDT as gBlocks. The cloning primers were also custom synthesized by IDT. The pRSF-1b plasmid was purchased from Novagen. The gene insert encoding mRuby3 was codon optimized and custom synthesized by IDT as a gBlock. The three TSGIT genes were independently cloned by Gibson assembly into empty pRSF-1b plasmids, yielding plasmids that are denoted herein as pTSGIT, pTSGIT-N and pTSGIT-C, respectively. The gene insert encoding mRuby3 (FIG. 2B—top panel) was cloned into pTSGIT between the SUMO and Intein regions by Gibson assembly. This plasmid is denoted herein as pTSGIT-mRuby3. All final constructs were verified by sequencing.

Protein Expression and Purification pTSGIT-N, pTSGIT-C and pTSGIT-mRuby3 were independently expressed in BL21(DE3) *E. coli* expression strain (Novagen) in LB media containing Kanamycin (50 μg/ml). Cell growth and lysis were performed as described previously[24]. Briefly, cells were collected by centrifugation and pellets were re-suspended in 5 ml lysis buffer [50 mM HEPES pH (8), 500 mM NaCl, 30 mM Imidazole, 0.1 mM Tris(2-carboxyethyl)phosphine hydrochloride (TCEP), 1 mM PMSF, 5% Glycerol and one EDTA-free protease inhibitor cocktail tablet per 50 ml (Roche, UK)] per 1 g of cells. The cells were then lysed by sonicating them twice on ice using a Qsonica 500 sonicator operating at 20 kHz, 37% amplitude with a cycle on-time of 10 s, a cycle off-time of 15 s and a total on-time of 2 min. Next, the lysates were passed twice through a French press operating at 20,000 psi and cleared by centrifugation at 95,834 g for 45 min at 4° C. All the subsequent protein purification steps were performed at 4° C.

All the affinity columns used for protein purification were HisTrap HP 5 ml and StrepTrap HP 5 ml affinity columns (GE Healthcare). The buffers used for protein binding, washing and elution for the HisTrap steps were buffer A [50 mM HEPES pH (8), 500 mM NaCl, 30 mM Imidazole, 0.1 mM TCEP and 5% Glycerol] and buffer B [50 mM HEPES pH (8), 500 mM NaCl, 350 mM Imidazole, 0.1 mM TCEP and 5% Glycerol]. The buffers used for protein binding, washing and elution for the StrepTrap steps were buffer C [50 mM HEPES pH (8.3), 500 mM NaCl, 0.1 mM TCEP and 5% Glycerol] and buffer D [50 mM HEPES pH (8.3), 500 mM NaCl, 2.5 mM d-Desthiobiotin, 0.1 mM TCEP and 5% Glycerol]. Cleavage reaction of the fusion protein was performed in cleavage buffer [50 mM HEPES pH (8.5), 500 mM NaCl, 10 mM 2-Mercaptoethanesulfonic acid (2-MESNA) and 5% Glycerol]. All the final protein fractions were stored in storage buffer [50 mM HEPES pH (8), 250 mM NaCl, 1 mM Dithiothreitol (DTT) and 5% Glycerol]. The same storage buffer was used to equilibrate and elute the proteins from a 120 ml Superdex 16/600 75 pg (GE Healthcare) column. Buffer exchange steps were performed using PD-10 desalting columns (8.3 ml of Sephadex G-25 medium; Amersham Biosciences). Capturing of the biotin-tagged proteins was performed using High Capacity NeutrAvidin Agarose Resin (Thermo Scientific). The buffer used to equilibrate, wash and elute the proteins from the NeutrAvidin Agarose Resin was storage buffer. An ÄKTA purifier fast protein liquid chromatography (FPLC) system (GE Healthcare) was used to perform all the column-based chromatographic steps.

Protein Sample Analysis

The purity of the eluted protein fractions was estimated by SDS-PAGE analysis as described previously[24,25], but with two modifications. First, the 5× electrophoresis sample buffer was changed to (10% SDS, 50 mM TCEP, 50% Glycerol, 250 mM Tris-HCl and 0.5% bromophenol blue dye, pH 6.8) to replace thiol-containing DTT with TCEP as reductant. Second, the samples were heated up at 96° C. only for 30 sec. These precautions were taken to ensure that the degree of Intein-mediated cleavage is not overestimated on SDS-PAGE[31,32] (for more information consult the manual of IMAPC kit, New England BioLabs, E6901S) and that SDS-PAGE sample preparation does not lead to significant Peptide Backbone Fragmentation[40] of the mRuby3 fluorescent protein of interest (for more information consult the manufacturer's description of commercially available purified Red Fluorescent Protein, Recombinant RFP, Cell Biolabs, STA-202). The samples were separated on 10% SDS-PAGE gels (Invitrogen NuPAGE 10% Bis-Tris gels, 10 wells and 1.0 mm thickness), run at 200 V for 1 hr in 1×MOPS SDS running buffer (Invitrogen Novex 20× NuPAGE MOPS SDS Running Buffer). The molecular weight ladder marker used for all SDS-PAGE gels was PageRuler Prestained Protein Ladder (Thermo Scientific, 26616).

The final yields and concentrations of pure mRuby3 and mRuby3-BioP were determined by A280 measurements using NanoDrop spectrophotometer (Thermo Scientific)[24,25]. The extinction coefficient for both mRuby3 and mRuby3-BioP was considered 27390 $M^{-1}$ $cm^{-1}$. The reported values of protein amount and concentration throughout the manuscript were the average and standard deviation generated by six repeated measurements of A280. SDS-PAGE gels were imaged using the iBright CL1000 system (Invitrogen) and quantification was performed using the built-in option for gel analysis of the ImageJ software.

For the samples exhibiting less than 90% purity for mRuby3 or less than 98% purity for gp2.5, the protein yields were estimated by using the Pierce BCA protein assay kit (Thermo Scientific) with a Bovine Serum Albumin (BSA) standard, similarly to the protocol previously described in 1, but under denaturing conditions (5% SDS, 1 mM DTT and heating up to 95° C. for 10 min) to eliminate mRuby's natural absorbance that can interfere with the A562 measurement. For gp2.5 samples, the measurement was performed identically as described in 1, without the requirement of denaturing conditions. Six serial dilutions of the samples of interest were prepared in denaturing buffer and mixed with working reagent as per manufacturer's instructions. For A562 absorbance measurements, the resulting test samples were placed in a clear bottom 96-well microplate (Corning) and absorbance was measured using a xMark Microplate Spectrophotometer (Bio-Rad) set to 562 nm. The BCA standard curve was fit to a linear dependence of A562 versus BSA concentration. The A562 measurements of the unknown samples were converted to protein concentrations by using this standard curve and by taking into account the dilution factor. All the reported protein yields and errors represent the average and the standard deviation of six measurements.

Intein-Mediated Protein Ligation Reaction

Intein-mediated protein ligation between activated mRuby3 protein and BioP (CDPEK$^{Biotin}$DS) peptide[31] was performed in IPL buffer [50 mM HEPES pH (8.5), 500 mM NaCl, 1 mM 2-MESNA and 5% Glycerol] at 4° C. for 12 hrs with gentle rotation. The BioP peptide-containing biotin attached to an internal lysine residue was custom synthesized by GenScript (85.2% purity). The ligation reaction contained 10 µM activated mRuby3 and 1 mM BioP.

Fluorescence Measurements

Steady-state fluorescence measurements for the mRuby3/NeutrAvidin$^{DyLight650}$ system were conducted at room temperature using Fluoromax-4 (HORIBA Jobin Yvon). All emission spectra were measured in storage buffer. In all cases, excitation was set to 520 nm and emission spectra were collected between 530 and 750 nm. Both excitation and emission slit widths were set to 5 nm. Measurements were recorded with an integration time of 0.2 s. The emission spectra were corrected by subtracting the background emission of a blank solution comprised of storage buffer. The reported spectra are the average of three independent replicates. The spectra were then corrected and normalized. NeutrAvidin$^{DyLight650}$ was purchased from Thermo Fisher Scientific.

Correction and Normalization of Emission Spectra

Steady state emission spectra for the mRuby3/NeutrAvidinDyLigth650 were collected as described in the Materials and Methods section of the main text. For all emission spectra, the excitation wavelength was fixed to $\lambda_{ex}$=520 nm. The concentrations of biotin-labeled mRuby3 and unlabeled mRuby3 were both fixed to 50 nM. Emission spectra of various concentrations of NeutrAvidinDyLigth650 were collected and corrected by blank subtraction. The resulting set of spectra is denoted as I. Emission spectra of various concentrations of NeutrAvidin$^{DyLigth650}$ in the presence of biotin-labeled mRuby3 and unlabeled mRuby3 were collected and corrected by blank subtraction. The resulted sets of spectra are denoted as $\tilde{I}_{bio}$ and $\tilde{I}_{unlabelled}$, respectively. Including their full dependence, the sets of emission spectra can be written as:

$$\begin{cases} I = I(\lambda_{ex} = 520 \text{ nm}; \lambda_{em}, c) \\ \tilde{I}_{bio} = \tilde{I}_{bio}(\lambda_{ex} = 520 \text{ nm}; \lambda_{em}, c) \\ \tilde{I}_{unlabled} = \tilde{I}_{unlabled}(\lambda_{ex} = 520 \text{ nm}; \lambda_{em}, c) \end{cases} \quad (1)$$

where $\lambda_{em}$ is the current emission wavelength and c is the current concentration of NeutrAvidin$^{DyLigth650}$. The contribution of emission of NeutrAvidinDyLigth650 at a given wavelength upon direct excitation at 520 nm, i.e. I($\lambda_{ex}$=520 nm; $\lambda_{em}$, c), was then subtracted from each spectrum.

Simultaneously, the spectra were normalized to a total area of 1 A.U. by integration. The resulting corrected and normalized emission spectra of biotin-labeled mRuby3 and unlabeled mRuby3, in the presence of various concentration of NeutrAvidin$^{DyLigth650}$, are given by:

$$\begin{cases} \hat{I}_{bio}(\lambda_{ex} = 520 \text{ nm}; \lambda_{em}, c) = \dfrac{\tilde{I}_{bio}(\lambda_{em}, c) - I(\lambda_{em}, c)}{\int [\tilde{I}_{bio}(\lambda_{em}, c) - I(\lambda_{em}, c)] d\lambda_{em}} \\ \hat{I}_{unlabeled}(\lambda_{ex} = 520 \text{ n}; \lambda_{em}, c) = \dfrac{\tilde{I}_{unlabeled}(\lambda_{em}, c) - I(\lambda_{em}, c)}{\int [\tilde{I}_{unlabeled}(\lambda_{em}, c) - I(\lambda_{em}, c)] d\lambda_{em}} \end{cases} \quad (2)$$

where integration is performed over the whole collected emission spectrum. The explicit dependence on the fixed excitation wavelength was omitted for the R.H.S. terms for simplicity. For any given NeutrAvidin$^{DyLight650}$ concentration, the fluorescence emission enhancement at $\lambda_{em}$=673 nm (i.e. the position of the emission maximum of NeutrAvidin$^{DyLigth650}$) was calculated for biotin-labeled mRuby3 and unlabeled mRuby3 relative to their emission spectrum in the absence of NeutrAvidin$^{DyLigth650}$[i.e. $\hat{I}_{bio}$ ($\lambda_{ex}$=520 nm, $\lambda_{em}$=673 nm; 0) and $\hat{I}_{unlabelled}$ ($\lambda_{ex}$=520 nm, $\lambda_{ex}$=673 nm; 0) respectively] as:

$$\begin{cases} \Delta \hat{I}_{bio}(\lambda_{ex} = 520 \text{ nm}, \lambda_{em} = 673 \text{ nm}; c) = \hat{I}_{bio}(c) - \hat{I}_{bio}(0) \\ \Delta \hat{I}_{unlabeled}(\lambda_{ex} = 520 \text{ nm}, \lambda_{em} = 673 \text{ nm}; c) = \\ \qquad \hat{I}_{unlabeled}(c) - \hat{I}_{unlabeled}(0) \end{cases} \quad (3)$$

where the explicit dependence on the fixed excitation and emission wavelengths was omitted for the R.H.S. terms for simplicity. In the case of biotin-labeled mRuby3, where significant enhancement was observed, the dependence of fluorescence enhancement in emission at 673 nm upon excitation at 520 nm, as a function of NeutrAvidin$^{DyLigth650}$ concentration [denoted as $\Delta\hat{I}_{bio}$(c)], was fitted to a Hill-type dependence, similar to the one described in[46], as:

$$\Delta \hat{I}_{bio}(c) = \Delta \hat{I}_{max} \times \frac{c^n}{K_{1/2}^n + c^n}, \quad (4)$$

where $K_{1/2}$, represents the monomeric concentration of NeutrAvidin$^{DyLigth650}$ at which half of the maximum emission enhancement ($\Delta\hat{I}_{ax}$) is produced and n represents the Hill coefficient.

Time-Resolved Fluorescence Measurements

Time-resolved fluorescence lifetime measurements were carried out using QuantaMaster 800 spectrofluorometer (Photon Technology International Inc.) equipped with a Fianuim supercontinuum fiber laser source (Fianium, Southampton, U.K.) operating at 20 MHz repetition rate as described previously 7,8. Arrival time of each photon was measured with a Becker-Hickl SPC-130 time-correlated single photon counting module (Becker-Hickl GmbH, Berlin, Germany). Measurements were collected under magic angle (54.7°) conditions and photons were counted using time to amplitude converter (TAC). To reduce the collection of scattered light, a longpass filter (550 nm) was placed at the emission side. In all measurements, 10,000 counts were acquired.

The instrument response function (IRF) was estimated using a Ludox colloidal silica suspension dissolved in water.

Measurements were recorded at room temperature in gp2.5 binding buffer [50 mM HEPES-KOH pH (7.5), 50 mM KCl, 10 mM MgCl2, 1 mM DTT, 5% Glycerol and 0.1 mg/mL BSA]. The samples were excited at 532 nm and emission was collected at 565 nm with 5 nm slit width for both the excitation and emission. Cy3-labeled ssDNA was kept at a limiting concentration of 50 nM. Increasing concentrations of gp2.5 were then added to the Cy3-ssDNAcontaining samples. The fluorophore lifetime decays were then obtained using FluoFit software package (PicoQuant) applying the IRF and fitted to two-exponential decays. The best fit was chosen based on reduced chi-square and randomness of the residuals. The final lifetimes at each gp2.5 concentration represent the mean of amplitude-averaged lifetimes 9 of three independent replicates. The increase in Cy3 fluorescence lifetime upon gp2.5 binding at various concentrations is reported as a difference in ns compared to the fluorescence lifetime of the Cy3-labeled oligo in the absence of protein. The resulting binding isotherms at various concentrations of gp2.5 (c) versus the increase in Cy3 fluorescence lifetime were fitted to Hill-type dependencies similar to the one presented in Eq. (4) as:

$$\Delta \tau(c) = \Delta \tau_{max} \times \frac{c^n}{K_d^n + c^n}, \quad (5)$$

where $K_d$ represents the monomeric concentration of gp2.5 at which half of the maximum fluorescence lifetime enhancement ($\Delta \tau_{max}$) is produced and n represents the Hill coefficient.

Yield and Purity of Intermediate Protein Samples

For the samples exhibiting less than 90% purity, the protein yields were estimated by using the Pierce BCA protein assay kit (Thermo Scientific) with a Bovine Serum Albumin (BSA) standard, similarly to the protocol previously described in, but under denaturing conditions (5% SDS, 1 mM DTT and heating up to 95° C. for 10 min) to eliminate mRuby's natural absorbance that can interfere with the A562 measurement. Six serial dilutions of the samples of interest were prepared in denaturing buffer and mixed with working reagent as per manufacturer's instructions. For A562 absorbance measurements, the resulting test samples were placed in a clear bottom 96-well microplate (Corning) and absorbance was measured using an xMark Microplate Spectrophotometer (Bio-Rad) set to 562 nm. The BCA standard curve was fit to a linear dependence of A562 versus BSA concentration. The A562 measurements of the unknown samples were converted to protein concentrations by using this standard curve considering the dilution factor. All the reported protein yields and errors represent the average and the standard deviation of the measurements.

Expression and Purification of His-Tagged Ulp1 SUMO Protease

The gene encoding Trx-SUMO-Ulp1-His as a fusion protein was custom synthesized by IDT as gBlock and cloned into a pRSF-1b plasmid by Gibson assembly. This plasmid is denoted as pTSUlp1. This expression plasmid was transformed into E. coli strain BL21 (DE3) competent cells (Novagen) and colonies were selected on LB-agar plates containing 50 m/ml Kanamycin. Ulp1 was overproduced by growing the transformed cells in 10 liters of 2xYT media (Teknova) supplemented with the same concentration of Kanamycin. Cells were grown at 37° C. to an OD600 of 1.0 and then protein expression was induced by the addition of 0.5 mM isopropyl β-Dthiogalactopyranoside (IPTG) and incubated further for 6 hr at 37° C. Cells were collected by centrifugation at 5,500 g for 10 min and re-suspended in lysis buffer [20 mM Tris pH (8), 300 mM NaCl, 20 mM Imidazole, 5 mM β-Mercaptoethanol, 10% Glycerol and one EDTA free protease inhibitor cocktail tablet per 50 ml (Roche, UK)]. All further steps were performed at 4° C.

Cells were lysed enzymatically by adding 2 mg/ml lysozyme and mechanically by sonication using the same cycle conditions describe in the main Materials and Methods section. Cell debris was removed by centrifugation (22,040 g, 45 min) and the clear supernatant was directly loaded onto a custom-assembled 30 ml His-affinity column filled with Ni-NTA Superflow resin (QIAGEN) preequilibrated with binding buffer [20 mM Tris pH (8), 300 mM NaCl, 20 mM Imidazole, 5 mM β-Mercaptoethanol and 10% Glycerol]. We have previously noticed that the use of HisTrap HP 5 ml affinity columns (GE Healthcare) rapidly saturated with Ulp1 and a high amount of protein was lost in the flow-through fraction. Therefore, we increased the volume of the column to the 30 ml custom-assembled one described above. The 30 ml column was then washed with 10 column volumes of binding buffer followed by gradient elution with 10 column volumes of elution buffer [50 mM Tris pH (8), 300 mM NaCl, 500 mM Imidazole, 5 mM β-Mercaptoethanol and 10% Glycerol]. The peak fractions were pooled and dialyzed overnight in a dialysis buffer [25 mM Tris pH (7.5), 150 mM NaCl, 1 mM DTT and 50% Glycerol], flash frozen and stored at −80° C.

During protein expression Trx-SUMO as an N-terminal fusion tag provides increased expression and solubility levels. Ulp1 cleaves itself from the fusion, while remaining attached to its C-terminal His-tag which is then used for purification. The Trx-SUMO cleaved tag will pass as flow-through in the His affinity column. The design of self-cleaving Ulp1 in fusion with N-terminal SUMO is inspired from 11. Ulp1 SUMO protease cleaved itself from the fusion in vivo prior to cell lysis. The typical yield of this method generates 50-100 mg of His-tagged Ulp1 from a 10 liters culture. The custom-purified Ulp1 SUMO protease purity is shown in Figure S 1. Under the mentioned storage conditions the protein can also be stored at −20° C. for several months while retaining activity.

Single-Molecule Flow-Stretching Bead Assay

The primed single-stranded DNA (ssDNA) substrate was generated by annealing circular M13mp18 ssDNA (New England BioLabs) to 100-fold excess of the 5'-Digoxigenin-CTAGAGGATCCCCGGGTACCGAGCTCGAAT-TCGTAATCA-Biotin-TGGTCAT-AGCTGTTTCCTGTGTG-3' (SEQ ID NO:25) primer (Integrated DNA Technologies), which contains two orthogonal attachment modifications and which upon hybridization to M13mp18 ssDNA generates an EcoR1 restriction site. The annealed DNA was linearized with EcoRI (New England BioLabs), and the reaction was stopped by EcoRI inactivation at 65° C. for 20 min. Excess unannealed primers and heat-inactivated EcoRI were removed by using a QIAquick PCR purification kit (QIAGEN). The final concentration of the DNA was quantified by using UV visible absorption spectroscopy at 260 nm with an extinction coefficient of 91801.1 mM-1 cm-1.

Figure 2A:
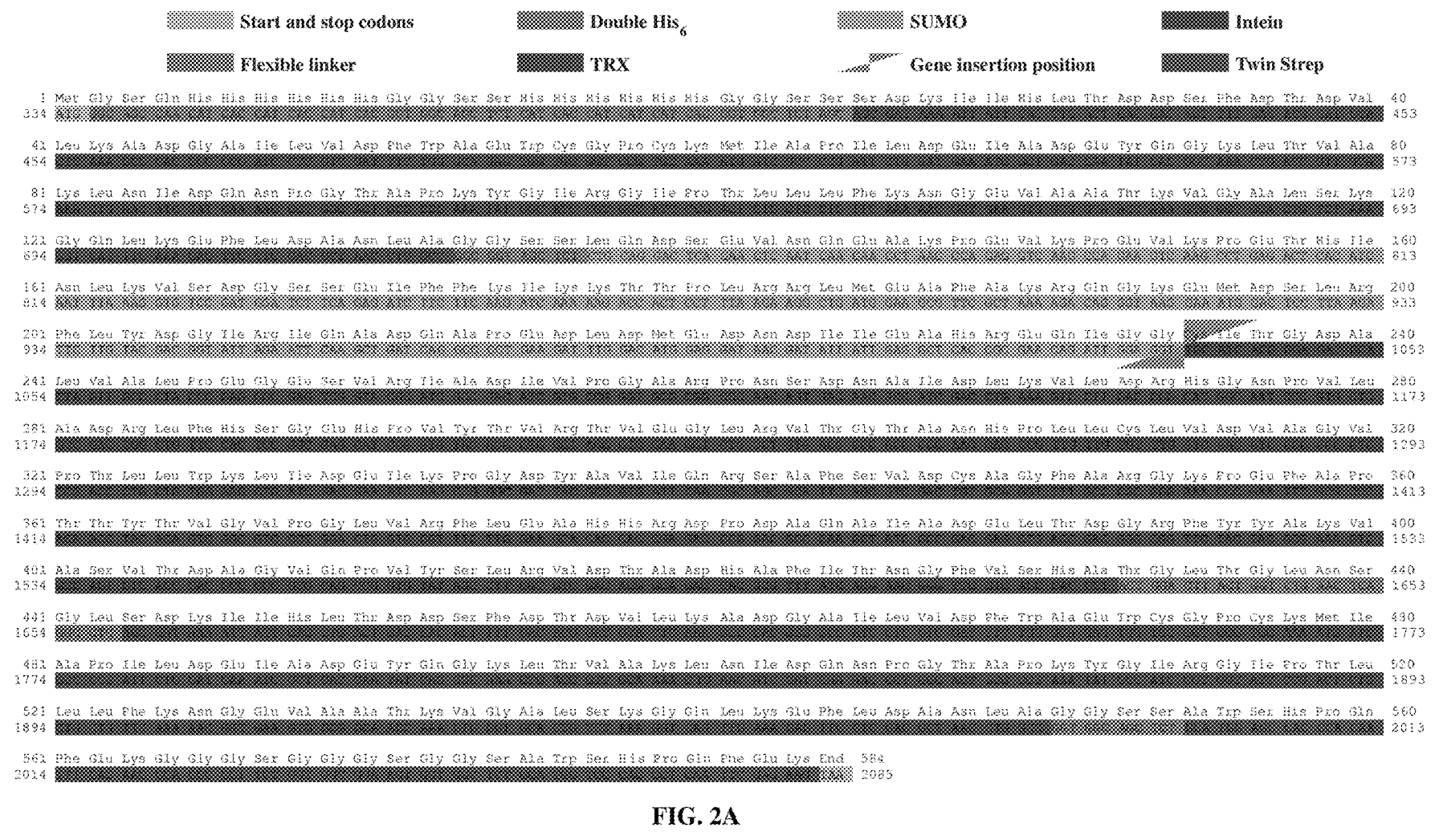
Figure 2B:
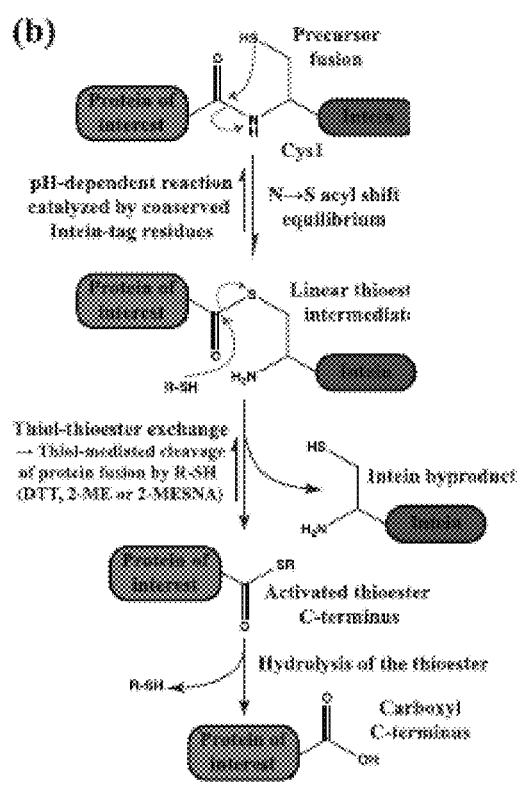
Figure 2C:
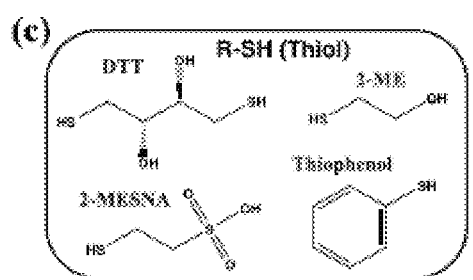
FIG. 2C shows the chemical structures of commonly employed thiol reagents for Intein-tag cleavage at its N-terminal junction.
Figure 2D:
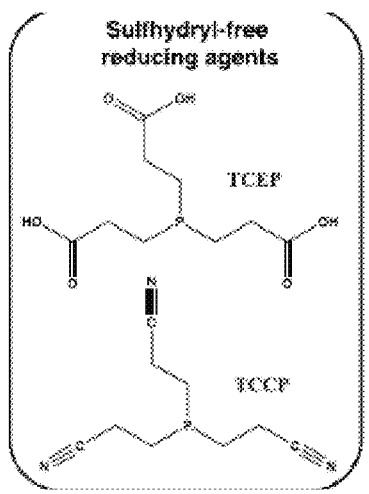
FIG. 2D shows chemical structures of sulfhydryl-free reducing agents.
Figure 2F:
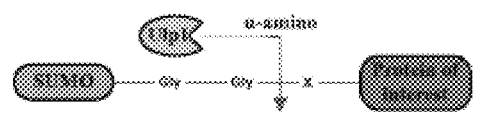
FIG. 2F is a schematic representation of the traceless cleavage of the SUMO-tag and therefore of the N-terminal fusion tag by the specific SUMO protease Ulp1 between the first amino acid of the protein of interest (X) and the second glycine residue of the C-terminal diglycine motif of SUMO.
Figure 2E:
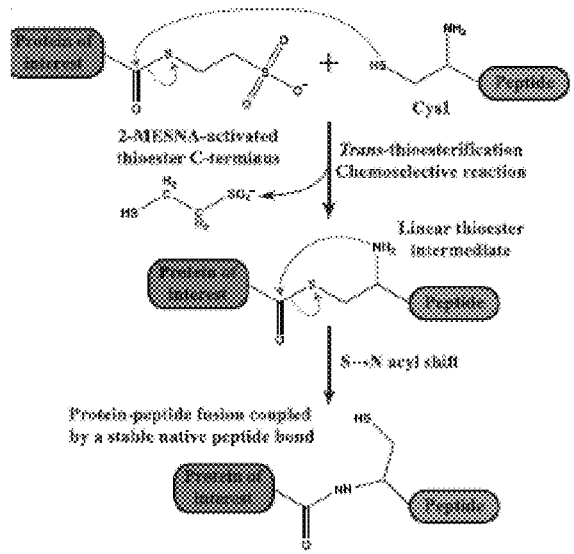
FIG. 2E is a schematic representation of the IPL reaction between a C-terminal 2-MESNA-activated protein of interest and a peptide that contains an N-terminal cysteine residue. Additional details about thiol-mediated Intein cleavage and IPL can be found in Supporting Information Material.

Single-molecule experiments were performed at room temperature in a custom-built microfluidic flow cell as described previously 12,13. Briefly, bacteriophage T7 ssDNA binding protein gp2.5 was introduced into the flow cell at concentration of 2 µM in T7 reaction buffer [40 mM Tris-HCl pH (7.5), 50 mM KGlu, 10 mM MgCl2, 10 mM DTT, and 0.1 mg/mL BSA]. The ssDNA stretching reaction was performed under continuous presence of protein in solution. Data acquisition and processing methods were identical to the previously described ones 14-16. The centroid position of the DNA-attached beads during each acquisition time point (500 ms sampling rate) was determined by fitting a 2-dimensional Gaussian distribution to the bead intensities by using the DiaTrack particle-tracking software (SemaSopht). Residual instabilities in the flow were corrected by subtracting traces corresponding to tethered DNA molecules that were not enzymatically altered. Displacement of the beads due to the conversion of the template strand from free ssDNA to gp2.5-coated ssDNA was transformed into the numbers of equivalent dsDNA base pairs (bp) by using a conversion factor of 3.76 bp/nm. This conversion factor was derived from the difference in the length between ssDNA and dsDNA at the applied stretching force of ~2.6 pN 15-17. General considerations on Intein-tag fusion cleavage This discussion is based on the chemical cascade scheme presented in FIG. 2b for thiol-cleavable contiguous mini-inteins. In the figure, Cys1 denotes the first cysteine residue of the Intein-tag. Briefly, the reaction is initiated by the peptide bond rearrangement between the last amino acid of the protein of interest and Cys1 of Intein-tag via N®S acyl shift in the precursor fusion protein. The resulting linear thioester intermediate can be attacked by the sulfhydryl group of a thiol reagent such as Dithiothreitol (DTT), β-Mercaptoethanol (2-ME), 2-Mercaptoethanesulfonic acid (2-MESNA), Thiophenol, or even free cysteine amino acid which results in cleavage of the Intein tag and therefore of the C-terminal fusion tag from the protein of interest via thiol-thioester exchange. The resulting protein of interest has an activated thioester C-terminus which is required for a subsequent IPL reaction. If IPL is not of interest and the excess free thiol reagent is removed, at basic pH, water can act as a nucleophile resulting in the hydrolysis of the activated thioester and formation of a native peptide carboxyl C-terminus. The reactions are driven forward (down in the scheme presented in FIG. 2b) toward the cleaved product by basic pH, presence of conserved Intein's B-block residues 1 (for Mxe GyrA amino acids TANH) and large excess of free thiol reagent (FIG. 2c). In this mechanism, basic pH aids the deprotonation of the sulfhydryl groups to increase their nucleophilic attack power, the conserved Intein's residues (especially H75) promote the initial N→S acyl shift, while excess thiol reagents provide the power for the thiol thioester exchange and prevent the re-ligation of the cleaved Intein-tag to the target protein. For the purification of oxidation-sensitive proteins, sulfhydryl-free reducing agents (FIG. 2d) can be used in buffer composition to maintain the cysteines of the protein of interest in their reduced form and prevent aggregation prior to the addition of the thiol reagent used for Intein-tag cleavage. If a thiol reducing agent would be included from the beginning of the protein purification, it can induce undesired premature cleavage of the fusion. In FIG. 2e, which shows the schematic representation of the cascade of chemical reactions of IPL, 2-MESNA is illustrated in its deprotonated form (sulfonate) as the reaction occurs at pH 8.5 above the pKa of its sulfo group. Finally, an S→N acyl shift component reaction of IPL ensures that the protein-peptide fusion is linked through a native peptide bond. The peptide can contain various modifications such as specific reactive groups or attachment moieties. The IPL reaction is typically driven forward by basic pH as described above and a high excess of peptide over target protein.

General Considerations on SUMO-Tag Fusion Design

The sequence encoding the gene of interest can be assembled together with the TSGIT N- and C terminal fusion tags by Gibson assembly cloning between the SUMO-tag and Intein-tag regions (FIG. 2a) into any desired destination plasmid. As most fusion systems, TSGIT does not require the inserted gene of interest to contain the N-terminal methionine since it already contains an initiator methionine at the N-terminus of the fusion. In E. coli, only one methionine aminopeptidase (MAP) exists 22. In general, removal of the initiator methionine by MAPs is based on the size of the residue immediately adjacent to the initiator methionine 22. If the initiator methionine-adjacent amino acid has a radius of gyration of 1.29 Å or less, then the initiation methionine will be cleaved by MAP. In fusion proteins, the N-terminal methionine encoded by the ATG codon of the inserted gene cannot be accessed by MAPs since it becomes a regular internal methionine rather than initiator methionine. If not manually removed, upon in vitro cleavage of the SUMO-tag by Ulp1, this methionine would be present at the N-terminus of the target protein and MAPs would not be present to ensure its removal. Failure to remove the initiator methionine can lead to dramatic decrease in protein activity. In general, the principle presented in 22 should be consulted to decide whether the first methionine should be included in the inserted gene. If the initiator methionine is removed, particular care should be taken in cases where the resulting cleaved protein of interest would have an N-terminal cysteine, as this residue can be attacked by the activated thioester C-terminus generated by Intein-tag cleavage, resulting in undesired circular protein forms and/or head-to-tail protein multimers.

Results and Discussion

The composite TSGIT system was tested in four steps. Initial studies verified if the N- and C-terminal parts of the fusion expressed correctly (FIG. 1). Second, mRuby3 fluorescent protein was purified using this optimized system as an example (FIG. 3). Next, studies verified that the IPL reaction proceeded efficiently for the purified mRuby3 (FIG. 3). In the last step, mRuby3 fluorescence was monitored using an energy-transfer assay that involved confirming both the functionality of mRuby3 through its fluorescence and the presence of the biotin moiety attached through IPL (FIG. 4). Finally, purified gp2.5 was purified using a tag-free protocol and using the TSGIT system, and showed that TSGIT had no effect on its oligomerization and activity (FIGS. 5A-5F and 6A-6D).

Design of the TSGIT System

The general scheme for using TSGIT is shown in FIG. 1A; a schematic representation and an amino acid sequence of TSGIT are provided in FIG. 1B and FIG. 2A, respectively. Several points were taken into consideration during the development of the fusion system. First, both the His and Strep affinity tags were included in their double form to improve the purification step (FIG. 1B). Second, a variety of flexible linkers were introduced between the individual elements of the fusion to increase the exposure and accessibility of each tag (FIG. 2A). Third, Trx-tags were introduced to both the N- and C-terminal parts of the fusion to ensure maximum solubility of these parts and of the fusion as a whole (FIG. 1B and FIG. 2A). For the cleavage tags, only two systems (SUMO and Inteins) are known not to leave additional undesired amino acids on the target protein after cleavage. Finally, SUMO and Intein are used as cleavable tags since they are two well-characterized structure-specific cleavable tags that do not leave additional undesired amino acids on the target protein after cleavage (traceless cleavage). The sequence encoding the gene of interest can be assembled together with the N and C-terminal fusion tags of TSGIT using Gibson assembly cloning between the SUMO and Intein regions into any desired destination plasmid (FIG. 2A).

The N-terminal SUMO cleavage tag was selected due to its small size and its efficient traceless cleavage reaction at its C-terminal junction (FIG. 2F), which occurs over a wide range of buffer conditions and relatively independent of the N-terminal amino acid sequence of the target protein of interest[23-25]. N-terminal Inteins could also be considered, since, similar to SUMO, their cleavage does not leave any additional undesired amino acids on the target protein. Nevertheless, as opposed to SUMO, they present several drawbacks. Thiol-cleavable Inteins such as the Sce VMA Intein are much larger in size, while the smaller Ssp DnaB Intein is cleaved by pH and temperature shift rather than reductants[32]. As for most Inteins, their cleavage efficiency is influenced by the terminal amino acids of the target protein[31,32] Moreover, another limitation is imposed by their cleavage, which can occur prematurely in an undesired fashion in vivo during the protein expression[31,32] Additionally, the shift to room temperature and the prolonged reaction time required by Ssp DnaB might be unsuitable for certain proteins. Finally, the N- and C-terminal combinations of the Ssp DnaB and Mxe GyrA or Mth RIR1 Inteins (implemented in the pTWIN1 and pTWIN2 expression vectors, New England BioLabs) have slightly different optimal pH preferences, which renders their efficient cleavage to be performed sequentially rather than simultaneously[32].

For the C-terminal part of the fusion, two complementary small-size Inteins can be used depending on the last amino acid of the target protein: Mxe GyrA and Mth RIR1[32]. These two Inteins are cleaved at their N-terminal junction (FIG. 2B, bottom panel) by sulfhydryl-containing (thiols, FIG. 2C) reagents reductants, among which 2-Mercaptoethanesulfonic acid (2-MESNA) and Thiophenol are preferred if a subsequent IPL reaction is required (FIG. 2E).[31]. While some of the aforementioned general drawbacks of Inteins are also true for Mxe GyrA and Mth RIR1, these represent the most competitive options available for C-terminal cleavage tags that do not generate extra amino acids after cleavage on the target protein. Mxe GyrA was incorporated rather than Mth RIR1 in the TSGIT design. Since its cleavage reaction occurs with a relatively high efficiency for C-terminal lysine or phenylalanine residues, such as the ones in our mRuby3 (FIG. 2B, top panel) or gp2.5 (FIG. 2B, middle panel) target proteins. As most inteins, naturally occurring Mxe GyrA39 can undergo cleavage at both of its termini. To block cleavage at its C-terminal junction, Mxe GyrA was engineered to carry the previously described N198A mutation (FIG. 2A). Removal of the C-terminal cyclization-capable asparagine residue blocks intermediate succinimide formation30 and consequently the cleavage at the Intein-tag C-terminal junction.

Figure 1C:
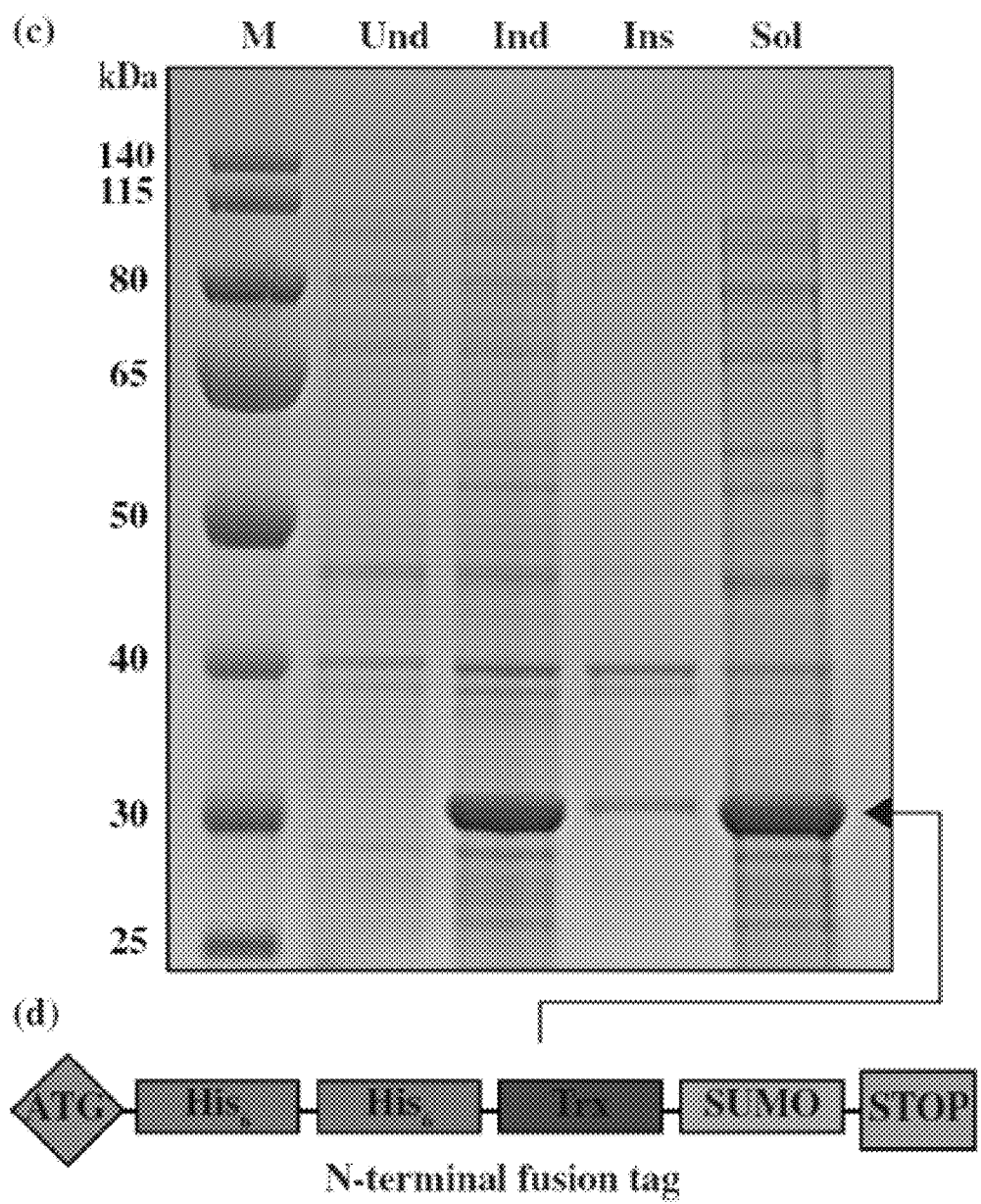
FIGS. 1C and 1D show induction and solubility controls for the (FIG. 1C) N-terminal and (FIG. 1D) C-terminal parts of TSGIT. SDS-PAGE gels showing the uninduced (Und), induced (Ind), soluble (Sol) and insoluble (Ins) samples for TSGIT-N and TSGIT-C.
Figure 1D:
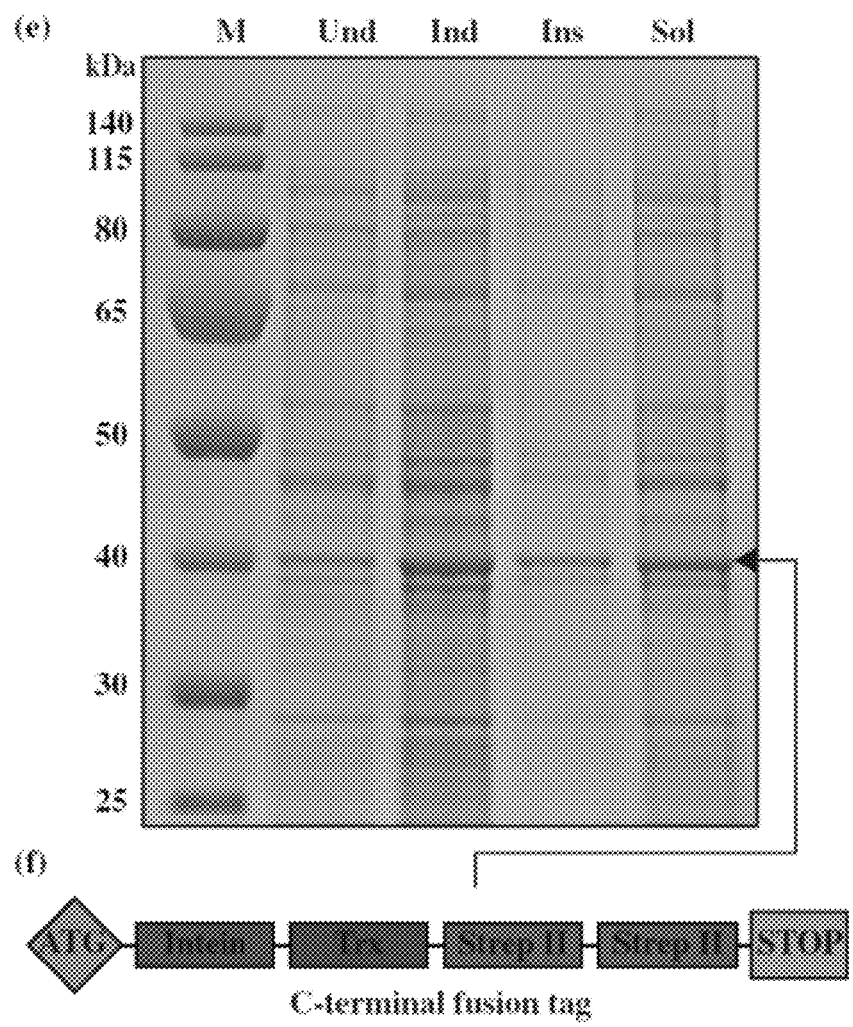

Once this design was determined, subsequent studies proceeded to verify the expression and solubility levels of the individual N- and C-terminal parts of TSGIT. Cultures of E. coli transformed with pTSGIT-N and pTSGIT-C were prepared as described in the Materials and Methods section. Upon induction of expression of pTSGIT-N, the N-terminal part of TSGIT, consisting of a double His-tag, Trx and SUMO, was immediately visible as a strong band in SDS-PAGE (FIG. 1C). After cell lysis and separation of the soluble and insoluble fractions, this part of the fusion was found to be mostly in the soluble form as desired. The same observations are made about the C-terminal part of the fusion, consisting of Intein, Trx and Twin Strep (FIG. 1d). Nevertheless, the expression level of the TSGIT C-terminal part was relatively lower than that of the N-terminal part, suggesting that the N-terminal Trx and SUMO tags were efficient in driving upward the expression level.

Together, these experiments showed that both the N- and C-terminal parts of TSGIT were not limiting for protein expression and solubility. The high expression level of the N-terminal part of the fusion was particularly desirable, as it could potentially drive forward the expression of the whole fusion. Moreover, the solubility of the individual parts of the fusion was also critical, both during the protein extraction phase and during purification, especially after cleavage. If the tags were insoluble on their own, cleavage might result in protein precipitation, which would negatively interfere with the downstream protein purification steps. It is worth noting that in cases where the protein of interest is large and reduction of the size of the construct is needed, the size of the fusion can be reduced by sequential removal of the Trx-tags, starting with the N-terminal one since SUMO can already cover on its own some of the benefits offered by Trx. If further reduction is needed, the His and Strep affinity tags can be reduced from their double to single versions.

Purification of mRuby3 Using the TSGIT System

Figure 3A:
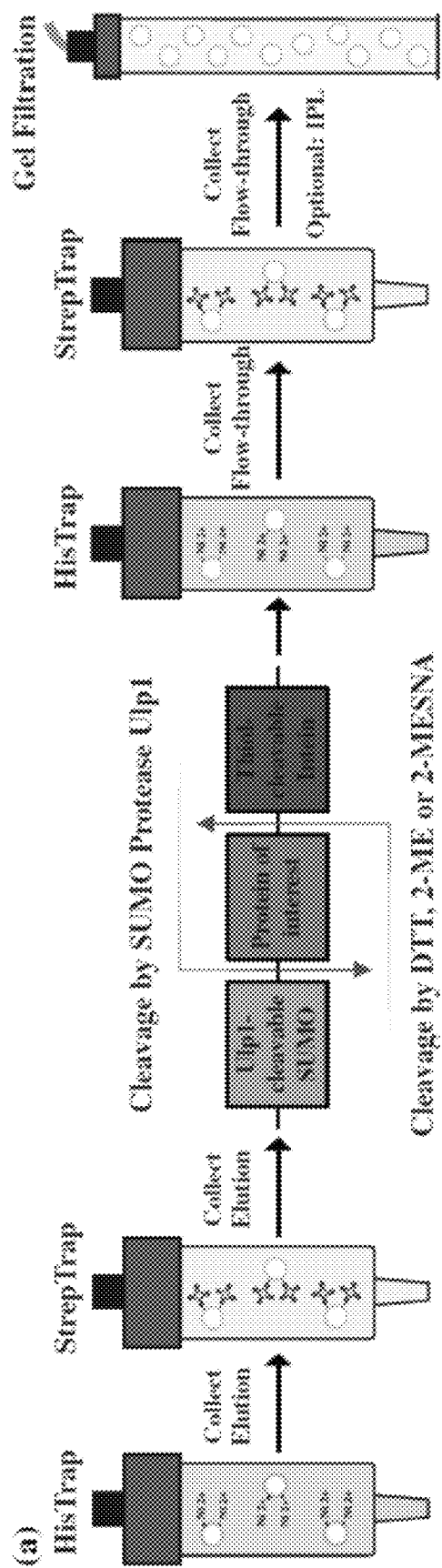
FIGS. 3A-3E show Purification of mRuby3 by employing TSGIT.
Figure 3B:
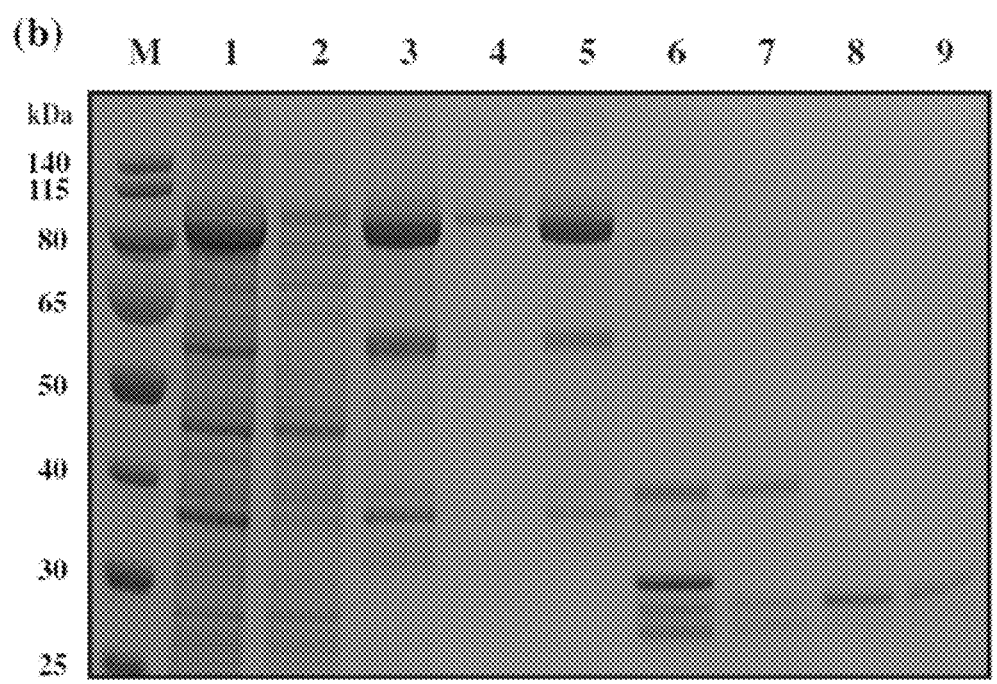

While SUMO has been used in a variety of applications in combination with His-tag, the C-terminal Intein, especially in commercially available plasmids, is often fused to a Chitin-binding domain tag (CBD-tag)[35,36]. Although the CBD-tag is suitable for on-resin bulk cleavage or denaturing elution conditions, its relatively strong binding makes it unsuitable for FPLC-based protein purification under native conditions when on-column cleavage is not desirable. To build a purification scheme that was fully FPLC-compatible, this tag was replaced with Twin Strep. The resulting purification scheme based on chromatography with His and Strep tags is shown in FIG. 3A. The success of this scheme was demonstrated by purifying mRuby3 fluorescent protein using TSGIT. The sequence encoding the gene of interest could be easily inserted into pTSGIT by Gibson assembly cloning between the SUMO and Intein regions (FIG. 2).

0.1 mM TCEP was included in the lysis and purification buffers in order to maintain a reducing environment prior to initiating Intein-tag cleavage by the addition of thiol reagents (FIG. 2B (bottom panel), FIG. 2C). Sulfhydryl-free reducing agents such as TCEP and TCCP (FIG. 2D) can provide efficient reducing conditions to prevent undesired disulfide bond formation, while their lack of sulfhydryl groups ensures that Intein cleavage reaction is not initiated prematurely. On the other hand, most of the thiols used to initiate the Intein cleavage reaction are also reducing agents (FIG. 2C) that will provide reducing conditions during the cleavage reaction.

The soluble fraction of the cell lysates for TSGIT-mRuby3 (lane 1 in FIG. 3B) was applied at a flow rate of 3 ml/min onto a 5-ml HisTrap affinity column pre-equilibrated with buffer A. This column was then washed with 15 column volumes (CV) of buffer A at a flow rate of 5 ml/min. The protein fusions were eluted with a 15 CV linear gradient of buffer B from 30 mM to 350 mM Imidazole (gradient of buffer B at a flow rate of 5 ml/min). The protein fusion eluted in a peak centered at ~210 mM Imidazole concentration (lane 3 in FIG. 3B). The eluted protein was then applied at a flow rate of 2 ml/min onto a 5-ml StrepTrap affinity column pre-equilibrated with buffer C. This column was then washed with 15 CV of buffer C at a flow rate of 5 ml/min. The protein fusions were eluted with a 15 CV linear gradient of buffer C from 0 mM to 2.5 mM d-Desthiobiotin (gradient of buffer D at a flow rate of 5 ml/min). The protein fusion eluted in a peak centered at ~0.85 mM d-Desthiobiotin concentration (lane 5 in FIG. 3B).

The protein was then concentrated to 2.5 ml using 10 kDa cut-off spin concentrators. Two PD-10 desalting columns were equilibrated three times with cleavage buffer. The concentrated protein was then passed through the PD-10 columns for rapid exchange of the buffer to 2-MESNA-containing cleavage buffer, to initiate cleavage of the C-terminal part of the fusion via Intein. Cleavage of the N-terminal SUMO-containing part of the fusion was initiated by addition of His-tagged SUMO protease Ulp1. Cleavage was allowed to continue overnight at 4° C. with gentle rotation.

Following incubation, cleavage was confirmed by SDS-PAGE (lane 6 in FIG. 3B) and 2-MESNA was removed by rapid buffer exchange to buffer A via two PD-10 columns. The cleaved His-tagged N-terminal part of the fusion, the His-tagged SUMO protease and any N-terminal uncleaved products were removed by passing the cleaved protein products through a second HisTrap affinity column; similarly to the first HisTrap affinity column, yet this time flow-through was collected (lane 7 in FIG. 3B). The cleaved Strep-tagged C-terminal part of the fusion and any C-terminal uncleaved products were removed by passing the cleaved protein products through a second StrepTrap affinity column; similarly to the first StrepTrap affinity column, yet this time flow-through was collected (lane 8 in FIG. 3B).

Figure 3C:
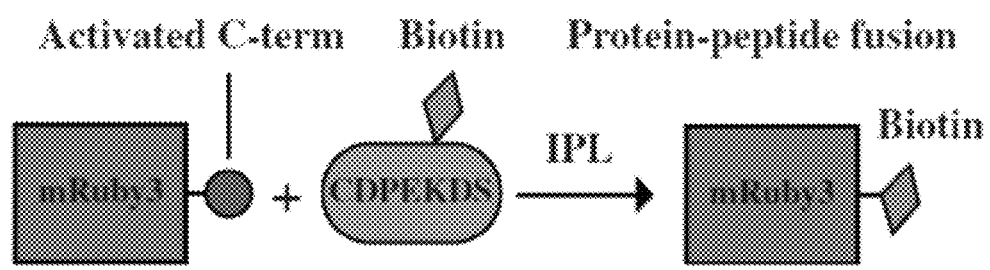
Figure 3D:
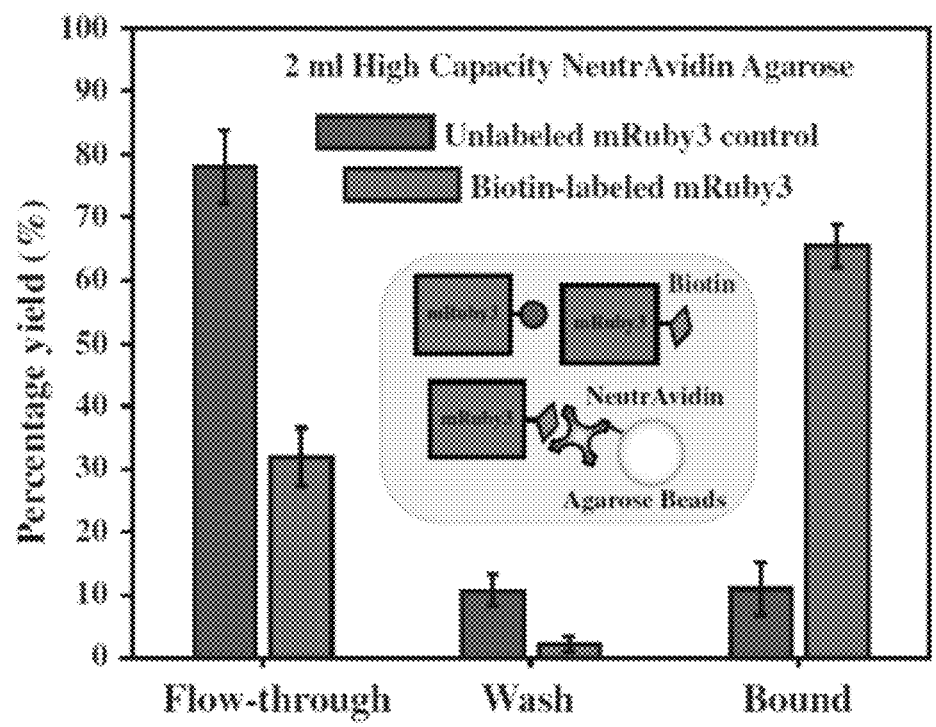
Figure 3E:
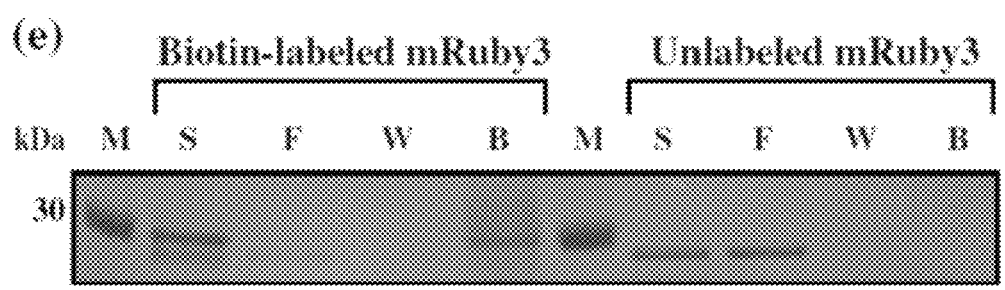
Figure 3F:
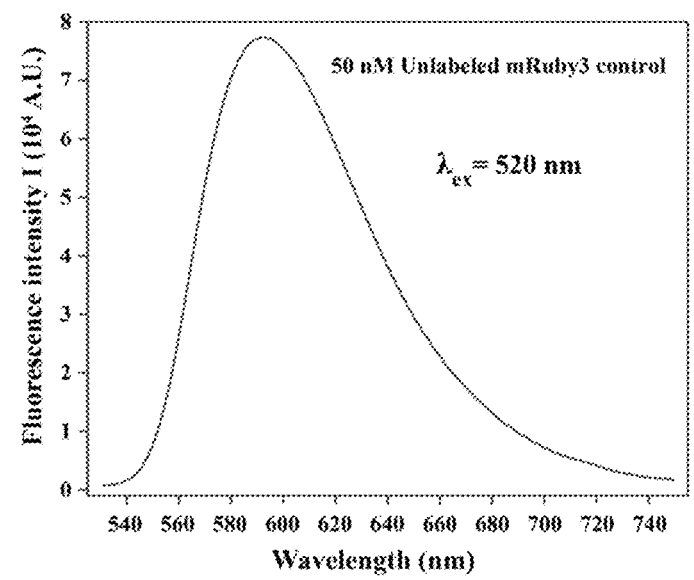
FIGS. 3F and 3G show fluorescence functionality of the final purified proteins. The emission spectra of (FIG. 3F) 50 nM unlabeled mRuby3 and (FIG. 3G) 50 nM IPL biotin-labeled mRuby3. All data points represent the average of three independent acquisitions. Both spectra were collected between 530 and 750 nm upon excitation at 520 nm.

The flow-through of this second StrepTrap affinity column contained more than 90% pure mRuby3 with both N- and C-terminal parts of the fusion cleaved and removed from the protein. The yield of the purified mRuby3 was 2.7±0.2 mg from 50 ml of resuspended expression cells. The yields and purities of the protein obtained from each purification step are summarized in Table 1.

rate of 1 ml/min to a 120 ml Superdex 75 pg size-exclusion column that was pre-equilibrated with 1.5 CV of storage buffer. The pure fractions were selected (lane 9 in FIG. 3B), concentrated to 1 ml using 10 kDa cut-off spin concentrators and flash-frozen for subsequent experiments. This size-exclusion step increased the purity of the protein to greater than 95%. The functionality of the protein was tested by verifying its emission spectra (FIG. 3F). This protein served as the negative control for the subsequent experiments involving the IPL-treated protein. It is denoted as unlabeled mRuby3.

Functionality of IPL-Ready mRuby3 Produced by TSGIT

The second fraction was used to verify whether the purified mRuby3 was IPL-ready, as offered by the C-terminal cleavage of the Intein tag[31,32]. Cleavage of this tag, especially in the presence of 2-MESNA as reducing agent, generates a reactive C-terminus for the protein of interest that can efficiently react with a peptide or protein containing an N-terminal cysteine residue forming a continuous backbone (FIG. 3C). To illustrate this IPL reaction for the proteins generated by TSGIT, mRuby3 as fused to a small peptide, BioP, containing a modified lysine residue fused to a biotin moiety and an N-terminal cysteine residue for attachment.

The second half of the fraction obtained from the flow-through of the second StrepTrap affinity column was concentrated to 2.5 ml using 10 kDa cut-off spin concentrators and buffer was rapidly exchanged to IPL buffer by using two PD-10 columns. The concentration of the protein was adjusted to 10 μM with IPL buffer and 1 mM BioP peptide in IPL buffer was then added. The IPL reaction was allowed to continue overnight at 4° C. with gentle rotation. Following incubation, the excess unreacted peptide was removed by applying the reaction mixture at a flow rate of 1 ml/min to a 120 ml Superdex 75 pg size-exclusion column that was pre-equilibrated with 1.5 CV of storage buffer. The pure

TABLE 1

Yields and purities obtained during the purification of mRuby3 by TSGIT.

| Purification step | Elution from first HisTrap column | Elution from first StrepTrap column | Cleavage via Ulp1 and 2-MESNA | Flow-through of the second HisTrap column | Flow-through of the second StrepTrap column | Elution from size-exclusion column |
|---|---|---|---|---|---|---|
| Purity (SDS-PAGE) | ~60% [a] | ~76% [a] | ~86% [b] / ~23% [a] | ~89% [b] / ~31% [a] | ~92% [a] | >95% [a] |
| Total protein (mg) | 25.9 ± 3.5 [c] | 21.4 ± 2.1 [c] | 18.6 ± 1.8 [c] | 12.5 ± 2.3 [c] | 2.7 ± 0.2 [d] | 1.1 ± 0.2 [d,e] |

For the samples exhibiting more than 90% purity, the proteins amounts were determined by A280 measurements using NanoDrop as described in the Materials and Methods section of the main text. For the samples exhibiting less than 90% purity, the proteins amounts were determined by A562 measurements using Pierce BCA protein assay as described above. All the values in the table have their source indicated as: [a] purity of the band of interest, [b] purity of the sum of the bands resulted from cleavage, [c] as determined by Pierce BCA protein assay, [d] as determined by A280 measurements and e as determined for unlabeled mRuby3 fraction (half amount).

Figure 3G:
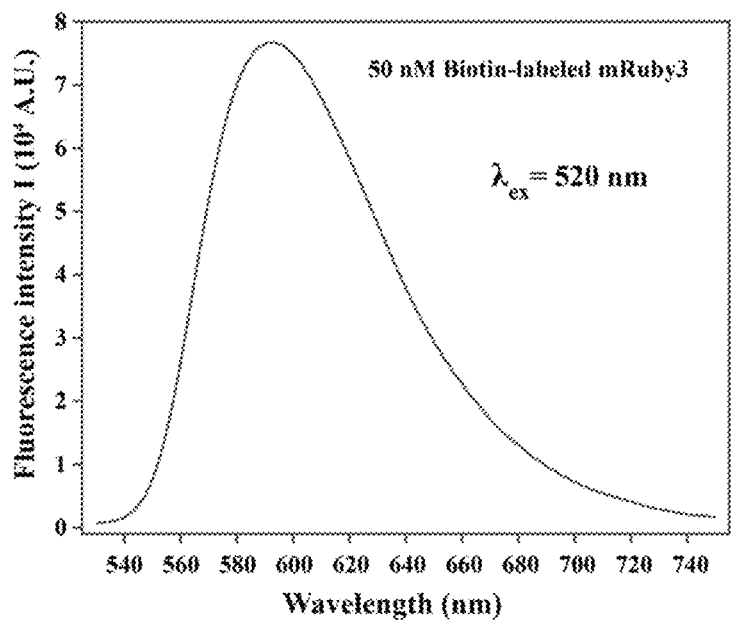

Following quantification, the protein prep was split into two equal fractions. One fraction was concentrated to 1 ml using 10 kDa cut-off spin concentrators and applied at a flow fractions were selected, concentrated to 1 ml using 10 kDa cut-off spin concentrators and flash-frozen for subsequent experiments. The functionality of the protein was tested by verifying its emission spectra (FIG. 3G). This protein is denoted this protein biotin-labeled mRuby3.

To test the efficiency of the IPL reaction and therefore of the addition of the biotin moiety to mRuby3, two preparations of 2 ml of NeutrAvidin Agarose resin were equilibrated three times with storage buffer; each time, the resin was settled by centrifugation and the supernatant was discarded. Solutions of 1 ml of 1 μM unlabeled mRuby3 and biotin-labeled mRuby3 were freshly prepared from the protein stocks in storage buffer. These protein solutions were then incubated with the NeutrAvidin Agarose preparations for 2 hrs at 4° C. The flow-through was separated by centrifugation. The resin containing the bound protein fusions was washed with storage buffer and then separated by centrifugation.

With the exception of the bound fraction, the yield of protein in each fraction was quantified by NanoDrop reading of A280 and converted to a percentage of the starting protein yield. The percentage yield for the bound fraction was estimated by subtracting the yield of the flow-through and wash fractions from the starting fraction because the presence of the large Agarose beads can interfere with its direct absorbance reading (FIG. 3D). Biotin-labeled mRuby3 bound with ~65% efficiency to the NeutrAvidin Agarose resin, while the unlabeled mRuby3 control bound with only ~10% efficiency, probably through unspecific binding. This binding enhancement clearly demonstrated the presence of the biotin moiety in the biotin-labeled mRuby3 due to the IPL reaction. Moreover, the same results could be directly visualized using SDS-PAGE (FIG. 3E). Additionally, SDS-PAGE showed that the ~35% of unbound biotin-labeled mRuby3 was generated by an incomplete IPL reaction. The IPL reaction and Intein cleavage have been previously shown to be strongly dependent on the C-terminal amino acid of the protein of interest[31,37]. Moreover, the efficiency of cleavage and IPL were shown to be able to increase with longer (up to 40 h) incubation times. Nevertheless, the IPL reaction time was intentionally restricted to only 12 hrs to capture this limitation.

Figure 4A:
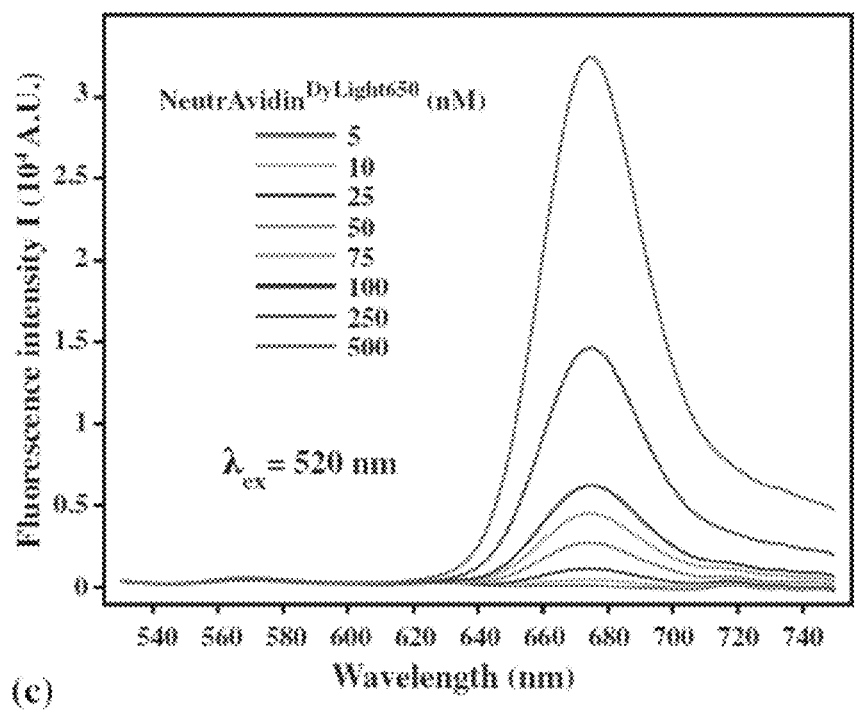
FIGS. 4A-4D show Fluorescence functionality of the TSGIT-purified mRuby3.
Figure 4B:
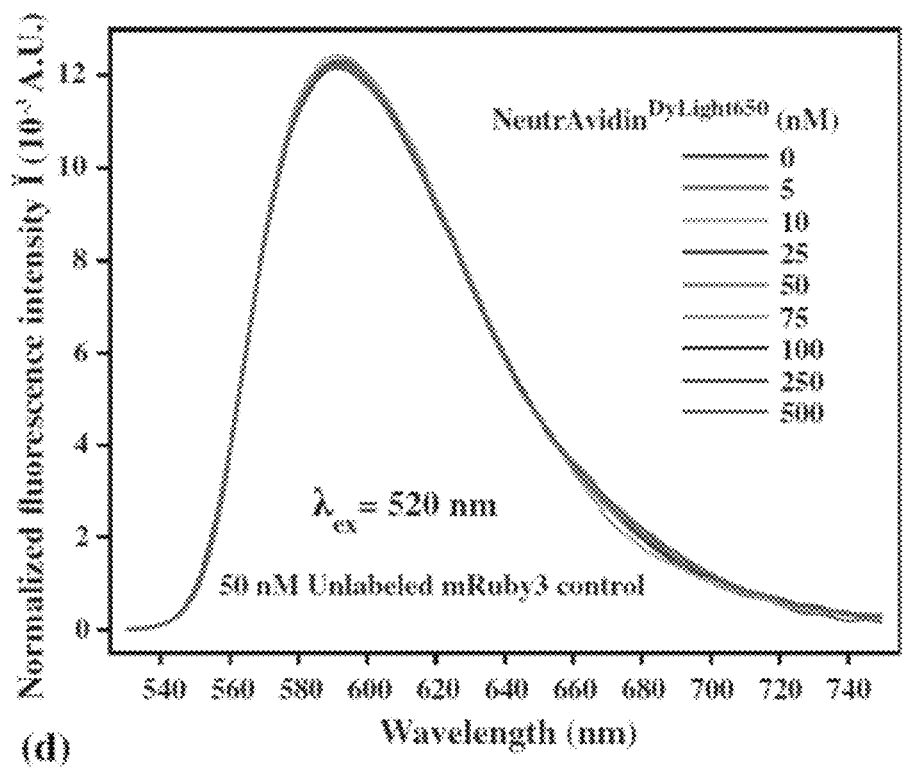

To directly test the fluorescence functionality of mRuby3 purified using TSGIT and the efficiency of the IPL reaction, subsequent studies designed an assay based on sensitized emission Førster resonance energy transfer (FRET)[38] between mRuby3 and NeutrAvidin$^{DyLight650}$. DyLight650 was selected as the acceptor since its excitation spectrum exhibits significant overlap with the emission spectrum of mRuby3. Solutions of 150 μl of 100 nM unlabeled mRuby3 and biotin-labeled mRuby3 were freshly prepared from the protein stocks in storage buffer. Solutions of 150 μl of various concentrations (10-1000 nM monomer) of NeutrAvidinDyLight650 were freshly prepared from protein stock in storage buffer. To account for the direct excitation at 520 nm of NeutrAvidin$^{DyLight650}$, the emission spectra of the solutions of various concentrations, mixed in equal volume with storage buffer, were recorded (FIG. 4A). Next, the solutions of unlabeled mRuby3 and biotin-labeled mRuby3 were mixed with solutions of various concentrations of NeutrAvidin$^{DyLight650}$. The emission spectra were collected for each sample, corrected for the direct excitation of NeutrAvidin$^{DyLight650}$ at the given concentration and normalized to a total area of 1 A.U.

Figure 4C:
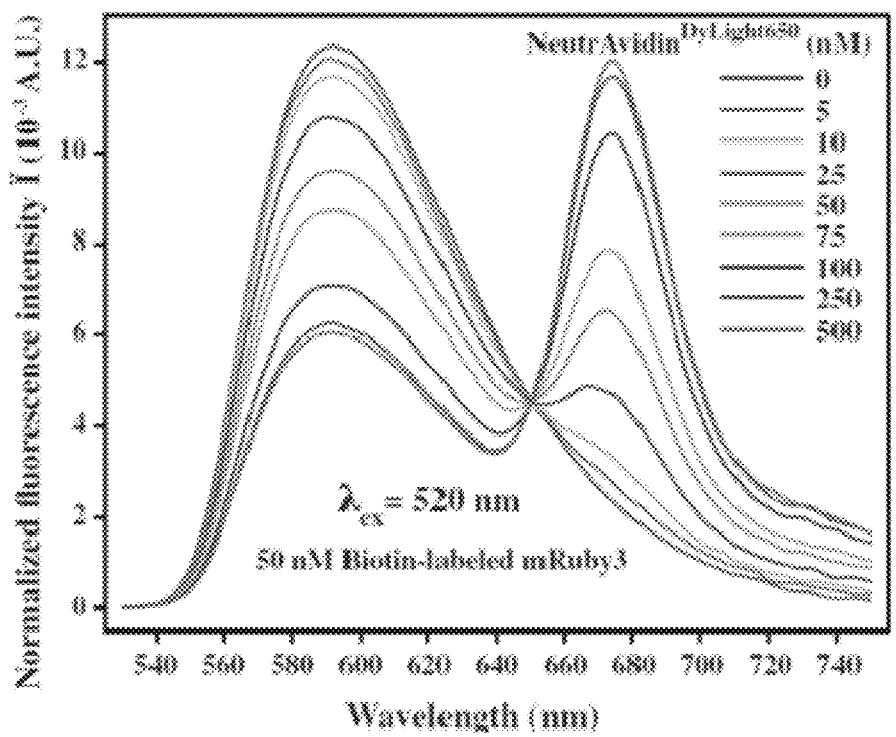
Figure 4D:
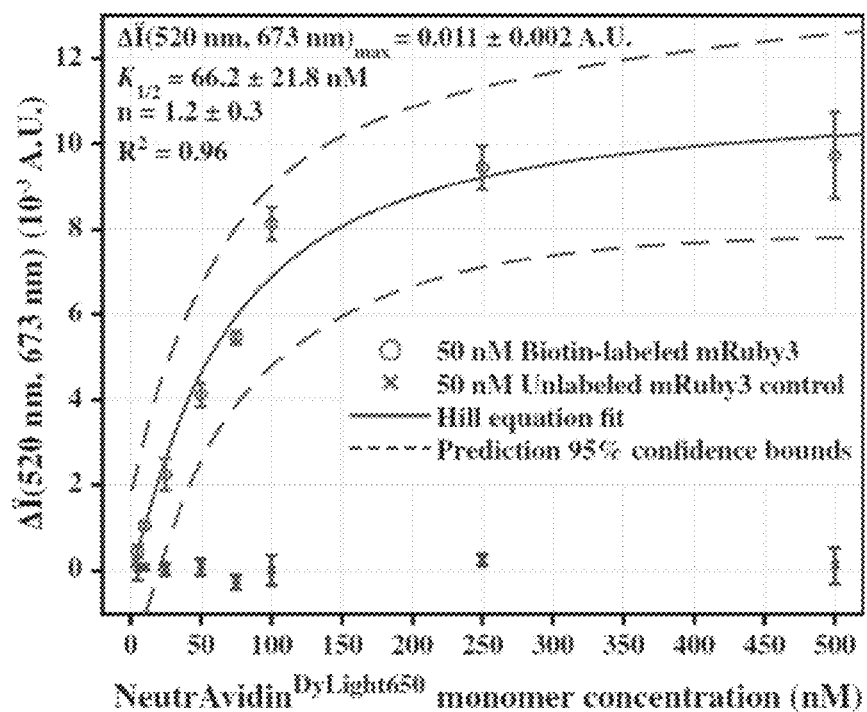

The signals from the samples containing unlabeled mRuby3 remained largely unchanged, beyond variations expected from experimental noise, upon addition of NeutrAvidin$^{DyLight650}$ (FIG. 4C), suggesting the absence of factors that would spatially constrain mRuby3 and NeutrAvidin$^{DyLight650}$ to be within FRET distance. On the contrary, for biotin-labeled mRuby3 produced by the IPL reaction, addition of increasing concentrations of NeutrAvidin-DyLight650 resulted in the emergence of a second emission peak centered at ~673 nm (FIG. 4C). Simultaneously, the amplitude of the direct emission of mRuby3, centered at ~592 nm, decreased in an anti-correlated manner with the increase in the emission of NeutrAvidin$^{DyLight650}$ (FIG. 4C), suggesting the efficient occurrence of FRET. When the increase in emission at 673 nm was plotted as a function of NeutrAvidin$^{DyLight650}$ concentration, the totally differing behaviors of unlabeled mRuby3 and IPL biotin-labeled mRuby3 became immediately obvious (FIG. 4D). Taken together, the FRET experiments clearly show that mRuby3 purified through TSGIT maintains its fluorescence functionality and that the IPL reaction proceeded properly allowing for biotin-labeling of the protein.

TSGIT-Purification of Gp2.5 ssDNA Binding Protein

Subsequent studies tested some of the potential limitation of TSGIT with respect to the effect of the tags on oligomerization and protein folding. We opted to use gp2.5 since it forms a stable dimer in solution36 and its ssDNA binding activity has been extensively characterized.36,44,45 TSGIT-gp2.5 was expressed and purified (FIG. 5A) as described for mRuby3 with two differences; cleavage of the C-terminal fusion via Intein-tag was initiated by DTT rather than 2-MESNA since no subsequent IPL was intended and the cleavage time was increased to 36 hr.

Figure 5A:
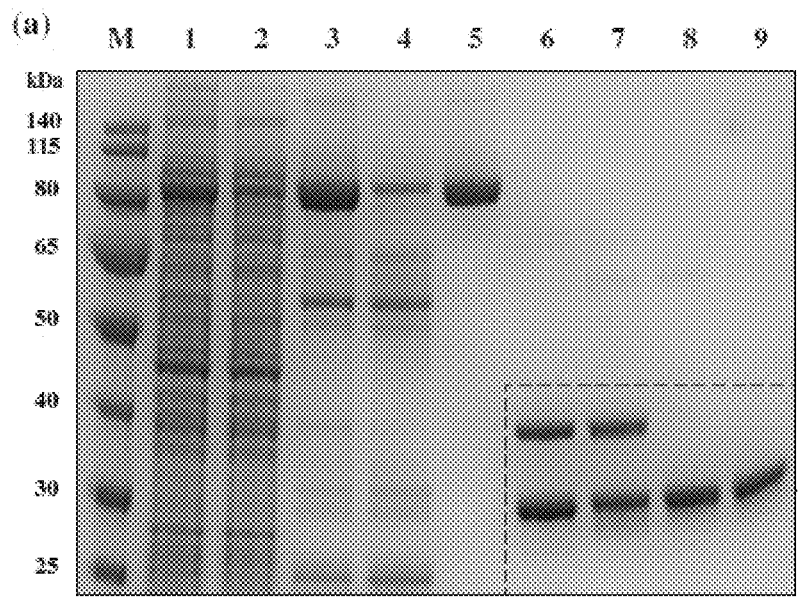
FIGS. 5A-5E show purification of gp2.5 by employing TSGIT and its microscopic characterization.
Figure 5B:
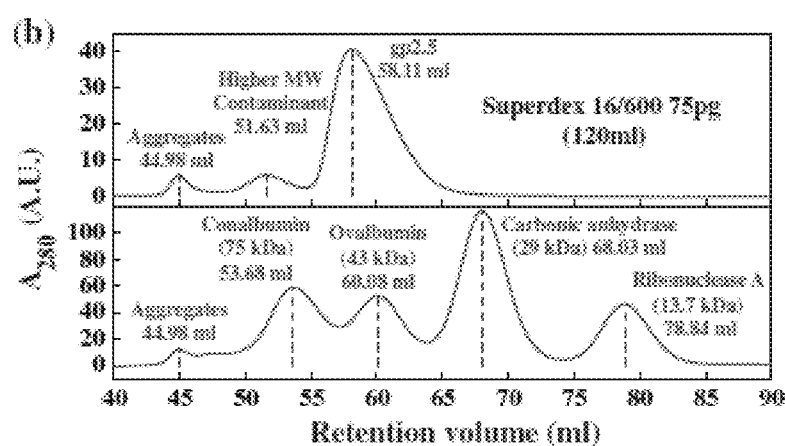
Figure 5C:
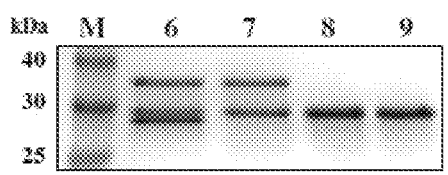

TSGIT-gp2.5 was eluted from the first HisTrap affinity column together with several contaminants (Lane 3 in FIG. 5A), which were removed efficiently by the subsequent StrepTrap affinity step (Lane 5 in FIG. 5A). The fusion was cleaved with high efficiency (Lane 6 in FIG. 5A,C) and the released N- and C-terminal fusion tags were removed by second HisTrap (Lane 7 in FIG. 5 A,C) and StrepTrap (Lane 8 in FIG. 5a,c) affinity steps. Finally, gp2.5 purity was polished using a Superdex 75 pg column (Lane 9 in FIGS. 5 A,C).

It is worth noting that due to their similar size and electrophoretic properties, the N-terminal fusion tag and gp2.5 could not be separated using the standard SDSPAGE conditions (Lane 6 in FIG. 5A). To separate them, the post-cleavage samples were analyzed using an increased percentage SDS-PAGE that was run at lower voltage for an increased amount of time as described in Supporting Information Materials and Methods section. The N-terminal fusion tag appeared as a slightly lower band than gp2.5 in Lane 6 in FIG. 5c, which was efficiently removed by the second HisTrap affinity step (Lane 7 in FIG. 5c). TSGIT-based purification of gp2.5 yielded ±4.3±0.1 mg from 35 mL of resuspended expression cells (7 g of dry cells) with a purity higher than 98% (Table 2).

TABLE 2

Yields and purities obtained during the purification of gp2.5 by TSGIT.

| Purification Step | Elution from first His Trap Column | Elution from first StrepTrap Column | Cleavage via Ulp1 and DTT | Flow-through of the second His Trap column | Flow-through of the second Strep Trap Column | Elution from size-exclusion column |
|---|---|---|---|---|---|---|
| Purity (SDS-PAGE) | ~67%[a] | ~96%[a] | ~97%[b]/~30%[a] | ~98%[b]/~60%[a] | ~98%[a] | >98%[a] |
| Total protein (mg) | 49.1 ± 2.6[c] | 29.3 ± 1.7[c] | 28.9 ± 0.1[c] | 18.0 ± 0.6[d] | 10.1 ± 0.2[d] | 4.3 ± 0.1[d] |

For the samples exhibiting more than 98% purity, the proteins amounts were determined by A280 measurements using NanoDrop as described above. For the samples exhibiting less than 98% purity, the proteins amounts were determined by A562 measurements using Pierce BCA protein assay as described above. All the values in the table have their source indicated as: [a] purity of the band of interest, [b] purity of the sum of the bands resulted from cleavage, c as determined by Pierce BCA protein assay and d as determined by A280 measurements.

Figure 7A:
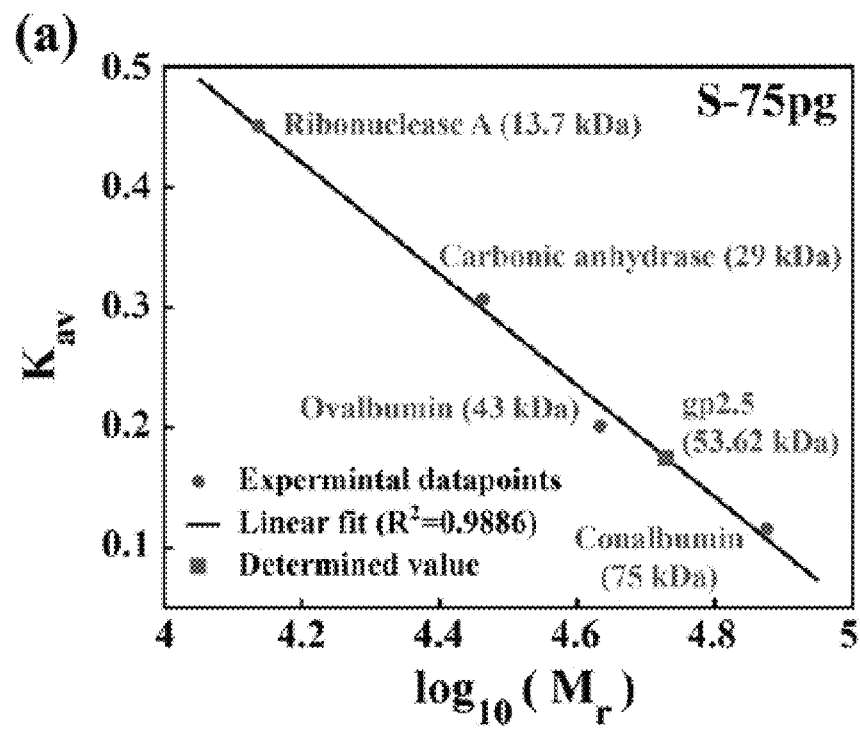
FIGS. 7A-7D. Characterization of the TSGIT-purified gp2.5.

Although this yield was ~3-fold lower than the one described in Reference 36, it was obtained without using very rich media or fermenter expression conditions. The solution dimerization state of TSGIT-purified gp2.5 was assessed by size-exclusion analysis using a Superdex 75 pg column pre-equilibrated and run with analysis Buffer. The gp2.5 monomer has a molecular weight of ~25.56 kDa as estimated from its amino acid sequence yet is known to run higher in SDS-PAGE.36 The retention volume of TSGIT-purified gp2.5 (FIG. 5b) was situated between the elution peaks of Conalbumin (~75 kDa) and Ovalbumin (~43 kDa), demonstrating that it formed a dimer in solution. Furthermore, using a calibration curve generated by the four known molecular weight calibration markers predicts a relative molecular weight of TSGIT-purified gp2.5 of ~53.62 kDa (FIG. 7a), which is consistent with the previously reported value of 53.7 kDa. These experiments demonstrate that TSGIT methodology did not interfere with gp2.5 dimerization.

Figure 7B:
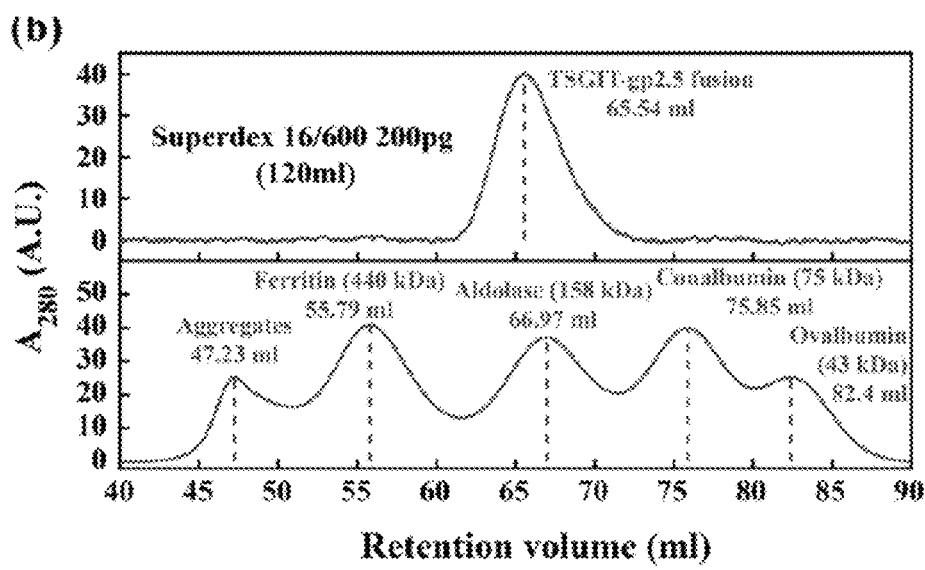
Figure 7C:
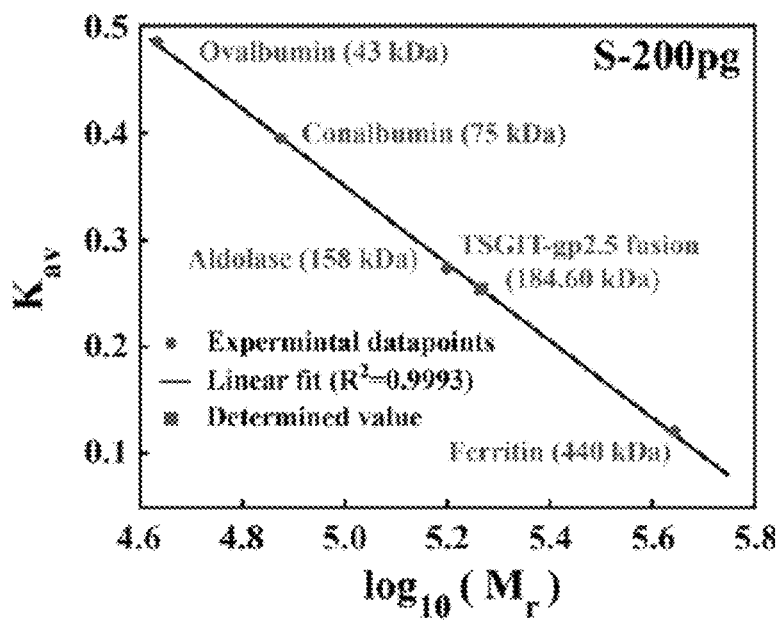

The complete size of the TSGIT-gp2.5 uncleaved fusion is ~88.42 kDa as estimated from its amino acid sequence. Performing a similar analysis as described above for the cleaved gp2.5 placed the uncleaved TSGITgp2.5 fusion molecular weight (FIG. 7b) in the vicinity of the Aldolase molecular weight calibration marker (~158 kDa) on Superdex 200 pg column. A calibration curve analysis estimated the relative molecular weight of the uncleaved TSGIT-gp2.5 to be ~184.6 kDa (-FIG. 7c), which is consistent with a dimer fusion protein rather than monomer. Remarkably, these results show that TSGIT fusion tags do not impair gp2.5 dimer formation neither before nor after fusion tags cleavage.

Figure 5D:
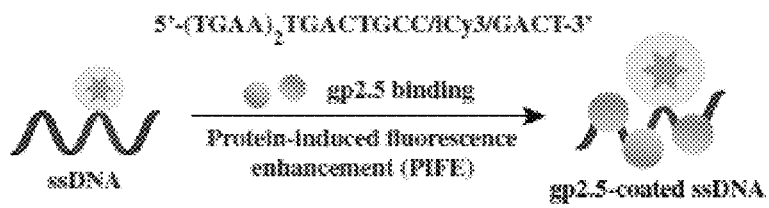

Subsequent studies sought to investigate if the TSGIT purification method had any impact on gp2.5 ssDNA binding activity. For comparison, we purified native tag-free gp2.5 as described previously.36 First, we investigated gp2.5 microscopic dissociation constant (Kd) as an indication of its affinity for ssDNA through a previously established protein-induced fluorescence enhancement (PIFE) assay. We selected a 21 nucleotide (nt) ssDNA sequence labeled internally with Cy3, which undergoes an increase in Cy3 fluorescence lifetime upon gp2.5 biding (FIG. 5d). Previous reports show that gp2.5 binds with a stoichiometry of one monomer per ~7 nt 36 and requires ~23 nt for stable binding. Therefore, ourCy3-ssDNA substrate can support the binding of up to three gp2.5 molecules.

Figure 5E:
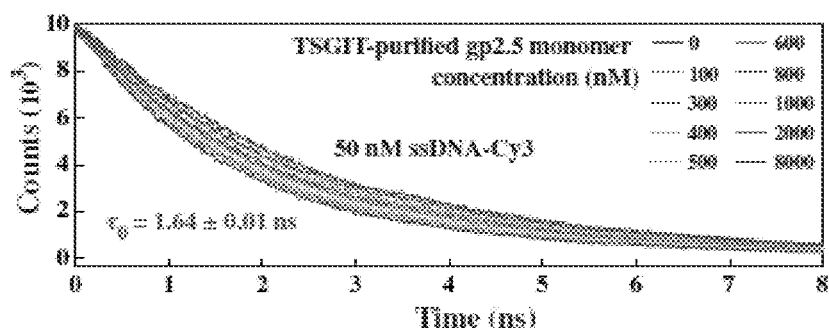
Figure 5F:
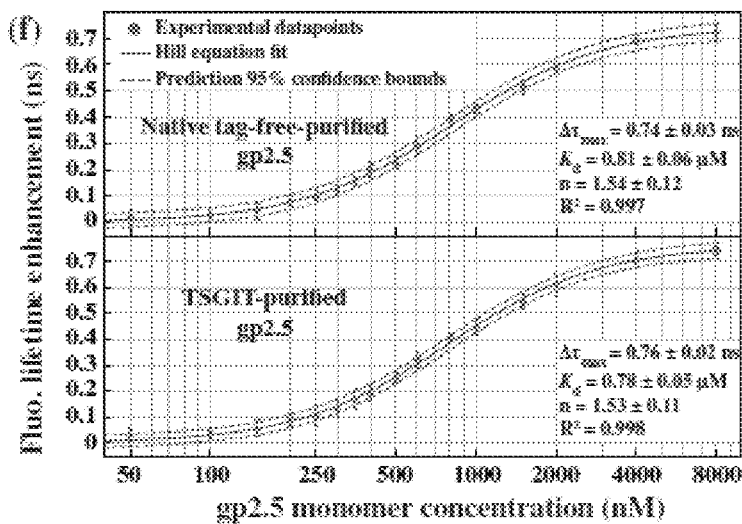
FIG. 5F shows binding isotherms (log-linear) of native tag-free-purified gp2.5 (top) and TSGIT-purified gp2.5 (bottom) to the Cy3-labelled ssDNA as determined from time-resolved fluorescence measurements. The y-axis represents the increase in Cy3 lifetime upon gp2.5 binding as compared to the lifetime of the oligo alone. All the elements of the plots have the same meaning as in FIG. 4D.
Figure 7D:
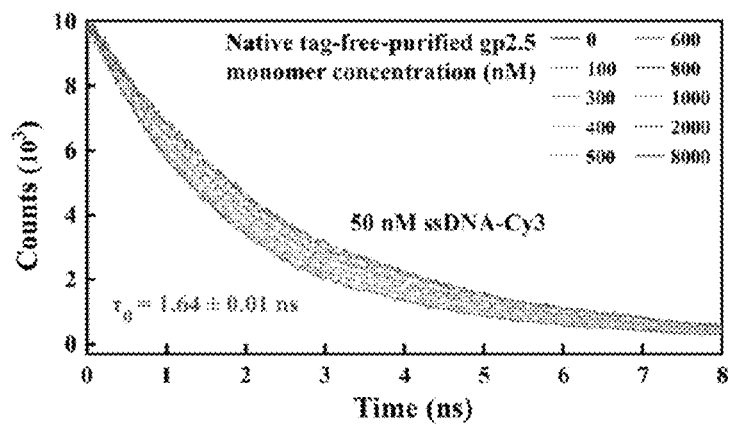

The lifetime of the oligo in the absence of protein was found to be ~1.64 ns (FIGS. 5e and 7d). Increased PIFE was observed upon protein titration for both TSGIT-purified gp2.5 and native tag-free-purified gp2.5 (FIGS. 5e and 7d). A plot of fluorescence lifetime versus ligand concentration servers as a binding isotherm, where the isotherm saturation value is proportional to the maximum achievable PIFE.47 Such plots were generated for both TSGIT-purified gp2.5 and native tag-free purified gp2.5 and the experimental datapoints were fit to a PIFE-adjusted Hill-type dependence (FIG. 5f) described by Equation (5) in Materials and Methods section. The Kd was calculated as ~0.78 μM for TSGIT-purified gp2.5 and ~0.81 μM for native tag-free-purified gp2.5 (FIG. 5f). These values are consistent with each other and with the previously reported value of ~0.8 μM.

Unlike other ssDNA-binding proteins, gp2.5 was previously reported to exhibit little binding cooperativity to ssDNA at any salt concentration. In accordance with this finding, the binding isotherms of both TSGIT purified gp2.5 and native tag-free-purified gp2.5 were characterized by a Hill coefficient of only ~1.5 (FIG. 5f) despite the length of the employed ssDNA which can support the binding of up to three gp2.5 molecules. It is worth noting that the sigmoidal shape of the binding isotherms is exaggerated since a log-linear plot is used to better illustrate the whole titration concentration range; even a perfect Langmuir hyperbolic isotherm would appear sigmoidal in log-linear plots. The last parameter of interest of the binding isotherms is the maximum increase in Cy3 fluorescence lifetime at saturating gp2.5 concentrations of ~0.76 ns for TSGIT-purified gp2.5 and ~0.74 ns for native tag-free-purified gp2.5 (FIG. 5f). Since the fluorescence lifetime is highly specific and sensitive to the nearby protein residues, their conformation as well as the overall structure of the DNA dye-protein complex, this finding further strengthens the similarity between TSGIT-purified gp2.5 and native tag-free-purified gp2.5 at microscopic scale.

Figure 6A:
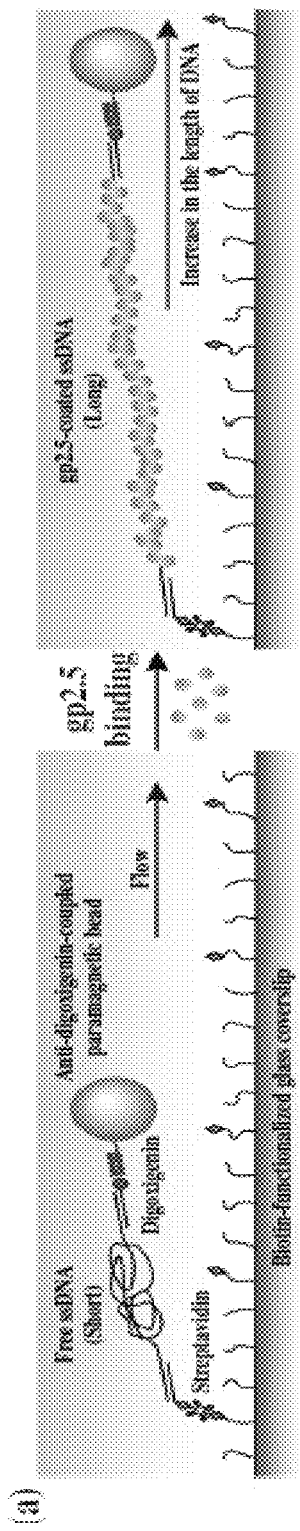
FIGS. 6A-6D show ssDNA stretching power of TSGIT-purified gp2.5.
Figure 6B:
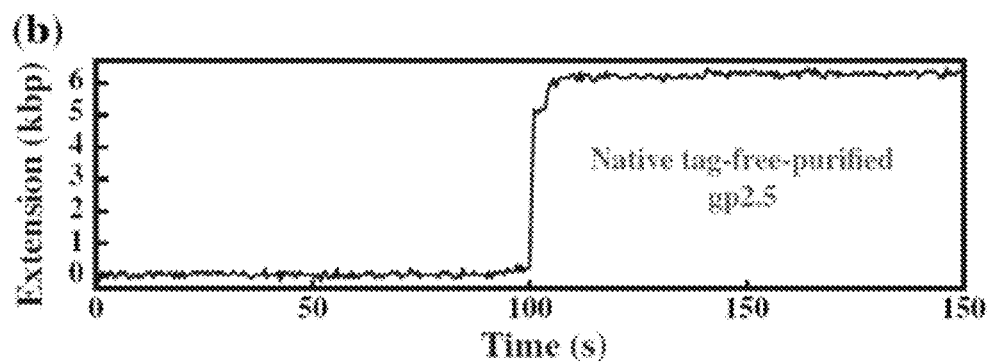
Figure 6C:
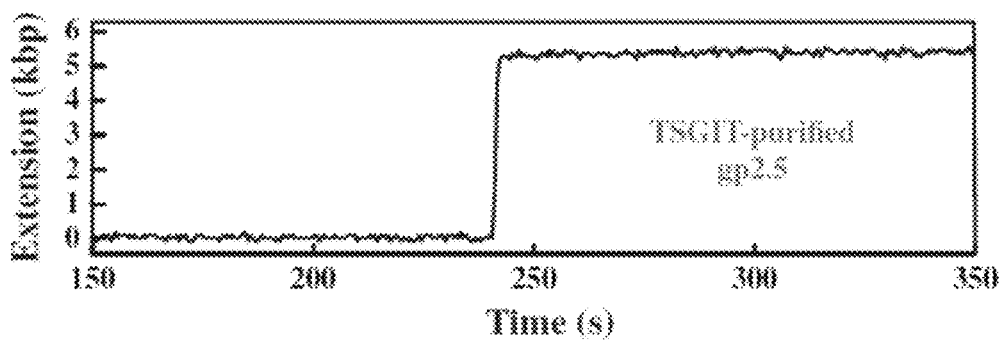
Figure 6D:
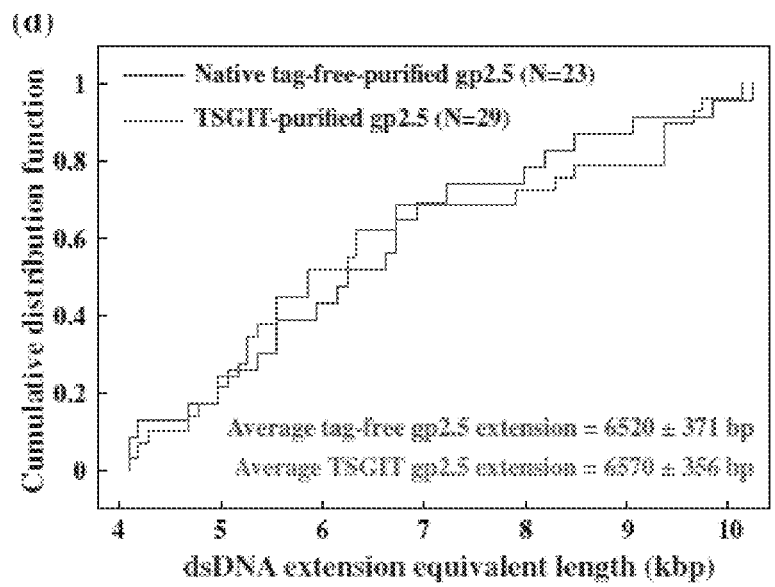
Figure 8A:
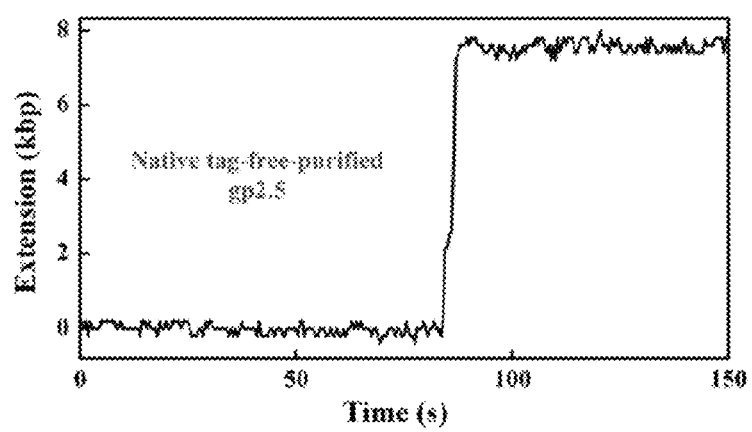
FIGS. 8A-8B show ssDNA stretching power of TSGIT-purified gp2.5.
Figure 8B:
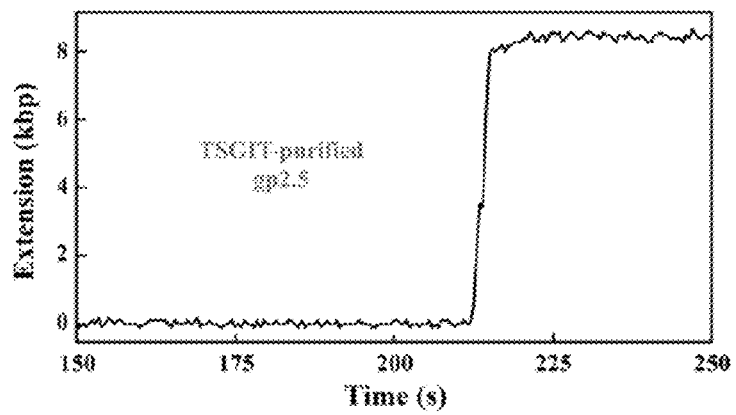

In the last set of experiments, we investigated TSGIT purified gp2.5 binding to ssDNA at a larger scale and its power to stretch collapsed ssDNA upon binding. The experiments are based on a well-established single molecule flow-stretching bead assay,44,50,51 which can monitor the conversion of free ssDNA to gp2.5-coated ssDNA via their length difference through the observation of the time-position dependence of a large bead attached to the free DNA end (FIG. 6a). The assay was performed as described in the Materials and Methods section using our previously described protocols 52,53. Native tag-free-purified gp2.5 (FIGS. 6b and 8a) and TSGIT-purified gp2.5 (FIGS. 6c and 8b) produced similar ssDNA stretching events; the stretching length is represented as equivalent length of dsDNA in base pairs (bp). Statistically, the distribution of the stretching lengths produced by native tag-free-purified gp2.5 and TSGIT-purified gp2.5 are highly similar (FIG. 6d) with their empirical cumulative distribution functions exhibiting less than 10% difference at any length. Both gp2.5 proteins stretched the ssDNA to an equivalent dsDNA length of ~6.5 kbp. The length of the ssDNA region of the employed substrate is ~7.2 knt. Therefore, we conclude that both TSGIT-purified gp2.5 and native tag-free-purified gp2.5 perform highly similar in this assay and stretch the ssDNA region of the substrate to 90% of the contour length of its equivalent dsDNA form, which is consistent with the previously reported value. Taken together, the gp2.5 experiments show that the protein obtained through TSGIT purification is virtually indistinguishable from the one obtained through native tag-free purification. Therefore, TSGIT purification, despite the presence of its large fusion tags did not disturb gp2.5 proper folding, its dimeric solution form or its ssDNA-binding activity. Nevertheless, as in the case of any fusion system, these results should be extrapolated with care to other proteins, for which the presence of the N- and C-terminal fusion tags may have a negative effect depending on the overall three-dimensional structure and folding of the fusion.

CONCLUSION

During protein expression and purification, a variety of mechanisms can generate soluble truncated forms of the protein of interest that coexist with the full-length form. These truncated forms can vary by different degrees from the protein of interest, and small N- or C-terminal degradations are typically inseparable from the full-length target protein under such conditions. A possible solution to this problem is the addition of at least one N-terminal and one different C-terminal affinity tag to form a fusion protein. Sequential selection for the two different affinity tags results in the exclusive retention of the full-length protein. Nevertheless, the presence of these tags can considerably interfere with the function of the protein and their removal is often desirable. TSGIT, a designed unified system for protein expression and purification that simultaneously resolves these problem, was designed. TSGIT also includes an N-terminal and a C-terminal Trx for increased solubility. TSGIT isolates the target protein between its N-terminal and C-terminal composite tags that are designed to maximize the benefits of each individual component. Upon simultaneous cleavage of these tags, the protein of interest is released without any undesired additional N- or C-terminal amino acids. The purification strategy proposed for TSGIT resulted in a high yield of more than 95% pure native protein of interest. Additionally, the purified protein produced by TSGIT is ready for IPL with other peptides or proteins for downstream applications. Through custom-synthesis, the peptides used for IPL can offer a large variety of modifications such as fluorophores, attachment groups (e.g. biotin and digoxigenin), glycans, localization sequences, and orthogonal reactive chemical groups for general coupling to different moieties (e.g. click chemistry), while having only the simple requirement to contain an N-terminal cysteine residue.

REFERENCES

1. Kimple M E, Brill A L, Pasker R L. Overview of affinity tags for protein purification. Curr Protoc Protein Sci 2013; 73:9 9 1-9 9 23.
2. Terpe K. Overview of tag protein fusions: from molecular and biochemical fundamentals to commercial systems. Appl Microbiol Biotechnol 2003; 60(5):523-33.
3. Costa S, Almeida A, Castro A, Domingues L. Fusion tags for protein solubility, purification and immunogenicity in *Escherichia coli*: the novel Fhb system. Front Microbiol 2014; 5:63.
4. Young C L, Britton Z T, Robinson A S. Recombinant protein expression and purification: a comprehensive review of affinity tags and microbial applications. Biotechnol J 2012; 7(5):620-34.
5. Waugh D S. An overview of enzymatic reagents for the removal of affinity tags. Protein Expr Purif 2011; 80(2): 283-93.
6. Frey S, Gorlich D. A new set of highly efficient, tag-cleaving proteases for purifying recombinant proteins. J Chromatogr A 2014; 1337:95-105.
7. Raran-Kurussi S, Cherry S, Zhang D, Waugh D S. Removal of Affinity Tags with TEV Protease. Methods Mol Biol 2017; 1586:221-230.
8. Ryan B J, Henehan G T. Overview of approaches to preventing and avoiding proteolysis during expression and purification of proteins. Curr Protoc Protein Sci 2013; Chapter 5:Unit5 25.
9. Jennings M J, Barrios A F, Tan S. Elimination of truncated recombinant protein expressed in *Escherichia coli* by removing cryptic translation initiation site. Protein Expr Purif 2016; 121:17-21.
10. Whitaker W R, Lee H, Arkin A P, Dueber J E. Avoidance of truncated proteins from unintended ribosome binding sites within heterologous protein coding sequences. ACS Synth Biol 2015; 4(3):249-57.
11. Rosano G L, Ceccarelli E A. Recombinant protein expression in *Escherichia coli*: advances and challenges. Front Microbiol 2014; 5:172.
12. Narayanan N, Chou C P. Alleviation of proteolytic sensitivity to enhance recombinant lipase production in *Escherichia coli*. Appl Environ Microbiol 2009; 75(16): 5424-7.
13. Wingfield P T. Overview of the purification of recombinant proteins. Curr Protoc Protein Sci 2015; 80:6 1 1-6 1 35.
14. Miller C G. Peptidases and proteases of *Escherichia coli* and *Salmonella typhimurium*. Annu Rev Microbiol 1975; 29:485-504.
15. Jankiewicz U, Bielawski W. The properties and functions of bacterial aminopeptidases. Acta Microbiol Pol 2003; 52(3):217-31.
16. Gonzales T, Robert-Baudouy J. Bacterial aminopeptidases: properties and functions. FEMS Microbiol Rev 1996; 18(4):319-44.
17. Lykkemark S, Mandrup O A, Friis N A, Kristensen P. Degradation of C-terminal tag sequences on domain antibodies purified from *E. coli* supernatant. MAbs 2014; 6(6):1551-9.
18. Parsell D A, Silber K R, Sauer R T. Carboxy-terminal determinants of intracellular protein degradation. Genes Dev 1990; 4(2):277-86.
19. Khan F, He M, Taussig M J. Double-hexahistidine tag with high-affinity binding for protein immobilization, purification, and detection on ni-nitrilotriacetic acid surfaces. Anal Chem 2006; 78(9):3072-9.
20. Fischer M, Leech A P, Hubbard R E. Comparative assessment of different histidine-tags for immobilization of protein onto surface plasmon resonance sensorchips. Anal Chem 2011; 83(5):1800-7.
21. LaVallie E R, Lu Z, Diblasio-Smith E A, Collins-Racie L A, McCoy J M. Thioredoxin as a fusion partner for production of soluble recombinant proteins in *Escherichia coli*. Methods Enzymol 2000; 326:322-40.
22. Xie Y G, Luan C, Zhang H W, Han F F, Feng J, Choi Y J, Groleau D, Wang Y Z. Effects of thioredoxin: SUMO and intein on soluble fusion expression of an antimicrobial peptide OG2 in *Escherichia coli*. Protein Pept Lett 2013; 20(1):54-60.
23. Panavas T, Sanders C, Butt T R. SUMO fusion technology for enhanced protein production in prokaryotic and eukaryotic expression systems. Methods Mol Biol 2009; 497:303-17.
24. Raducanu V S, Tehseen M, Shirbini A, Raducanu D V, Hamdan S M. Two chromatographic schemes for protein purification involving the biotin/avidin interaction under native conditions. J Chromatogr A 2020:461051.
25. Tehseen M, Raducanu V S, Rashid F, Shirbini A, Takahashi M, Hamdan S M. Proliferating cell nuclear antigen-agarose column: A tag-free and tag-dependent tool for protein purification affinity chromatography. J Chromatogr A 2019; 1602:341-349.
26. Bornhorst J A, Falke J J. Purification of proteins using polyhistidine affinity tags. Methods Enzymol 2000; 326: 245-54.
27. Schmidt T G, Batz L, Bonet L, Carl U, Holzapfel G, Kiem K, Matulewicz K, Niermeier D, Schuchardt I, Stanar K. Development of the Twin-Strep-Tag® and its application for purification of recombinant proteins from cell culture supernatants. Protein Expr Purif 2013; 92(1): 54-61.

28. Ivanov K I, Basic M, Varjosalo M, Makinen K. One-step purification of twin-strep-tagged proteins and their complexes on strep-tactin resin cross-linked with bis(sulfosuccinimidyl) suberate (BS3). J Vis Exp 2014 (86).
29. Evans T C, Jr., Benner J, Xu M Q. Semisynthesis of cytotoxic proteins using a modified protein splicing element. Protein Sci 1998; 7(11):2256-64.
30. Southworth M W, Amaya K, Evans T C, Xu M Q, Perler F B. Purification of proteins fused to either the amino or carboxy terminus of the *Mycobacterium xenopi* gyrase A intein. Biotechniques 1999; 27(1):110-4, 116, 118-20.
31. Burgess-Brown N A. Heterologous gene expression in *E. coli*: methods and protocols. New York, N.Y.: Humana Press; 2017. xiv, 429 pages p.
32. Xu M Q, Evans T C, Jr. Purification of recombinant proteins from *E. coli* by engineered inteins. Methods Mol Biol 2003; 205:43-68.
33. Xu M Q, Paulus H, Chong S. Fusions to self-splicing inteins for protein purification. Methods Enzymol 2000; 326:376-418.
34. Bajar B T, Wang E S, Lam A J, Kim B B, Jacobs C L, Howe E S, Davidson M W, Lin M Z, Chu J. Improving brightness and photostability of green and red fluorescent proteins for live cell imaging and FRET reporting. Sci Rep 2016; 6:20889.
35. Mitchell S F, Lorsch J R. Protein Affinity Purification using Intein/Chitin Binding Protein Tags. Methods Enzymol 2015; 559:111-25.
36. Bernard M P, Cao D, Myers R V, Moyle W R. Tight attachment of chitin-binding-domain-tagged proteins to surfaces coated with acetylated chitosan. Anal Biochem 2004; 327(2):278-83.
37. Goulatis L I, Ramanathan R, Shusta E V. Impacts of the −1 Amino Acid on Yeast Production of Protein-Intein Fusions. Biotechnol Prog 2019; 35(1):e2736.
38. Qian J, Yao B, Wu C. Fluorescence resonance energy transfer detection methods: Sensitized emission and acceptor bleaching. Exp Ther Med 2014; 8(5):1375-1380.
39. Braakman I, Helenius J, Helenius A. Manipulating disulfide bond formation and protein folding in the endoplasmic reticulum. EMBO J 1992; 11(5):1717-22.
40. Barondeau D P, Kassmann C J, Tainer J A, Getzoff E D. Understanding GFP posttranslational chemistry: structures of designed variants that achieve backbone fragmentation, hydrolysis, and decarboxylation. J Am Chem Soc 2006; 128(14):4685-93.
41. Mormann M, Eble J, Schwoppe C, Mesters R M, Berdel W E, Peter-Katalinic J, Pohlentz G. Fragmentation of intra-peptide and inter-peptide disulfide bonds of proteolytic peptides by nanoESI collision-induced dissociation. Anal Bioanal Chem 2008; 392(5):831-8.
42. Gorman J J, Wallis T P, Pitt J J. Protein disulfide bond determination by mass spectrometry. Mass Spectrom Rev 2002; 21(3):183-216.
43. Block H, Maertens B, Spriestersbach A, Brinker N, Kubicek J, Fabis R, Labahn J, Schafer F. Immobilized-metal affinity chromatography (IMAC): a review. Methods Enzymol 2009; 463:439-73.
44. Spriestersbach A, Kubicek J, Schafer F, Block H, Maertens B. Purification of His-Tagged Proteins. Methods Enzymol 2015; 559:1-15.
45. Gradia S D, Ishida J P, Tsai M S, Jeans C, Tainer J A, Fuss J O. MacroBac: New Technologies for Robust and Efficient Large-Scale Production of Recombinant Multiprotein Complexes. Methods Enzymol 2017; 592:1-26.
46. Leavesley S J, Britain A L, Cichon L K, Nikolaev V O, Rich T C. Assessing FRET using spectral techniques. Cytometry A 2013; 83(10):898-912.
47. Raducanu V S, Tehseen M, Shirbini A, Raducanu D V, Hamdan S M. Two chromatographic schemes for protein purification involving the biotin/avidin interaction under native conditions. J Chromatogr A 2020:461051.

---

We claim:

1. A fusion protein comprising a SUMO protease cleavable peptide and an intein sequence, wherein the fusion protein is represented by Formula III:

$$Ls\text{-}P_{1n}\text{-}L_{1a}\text{-}S_1\text{-}L_{1b}\text{-}D_1\text{-}L_1\text{-}B\text{-}L_2\text{-}D_2\text{-}L_{2b}\text{-}S_2\text{-}L_{2a}\text{-}P_{2n};$$

where:
Ls is a peptide linker;
in $P_{1n}$, $P_1$ is a first purification tag with n occurrences, where n is an integer ranging from 1-6;
$S_1$ is a first solubilization tag;
$L_{1a}$ is peptide linker between the first solubilization tag and the first purification tag;
$D_1$ comprises a SUMO protease cleavable peptide;
$D_2$ comprises the intein sequence;
$L_{1b}$ is a peptide linker between the first solubilization tag and the SUMO protease cleavage tag;
B is a target protein sequence;
$L_1$ is an optional linker between the SUMO protease cleavage tag and the target protein sequence;
$L_2$ is an optional linker between intein sequence and the target protein sequence;
$S_2$ is a second solubilization tag;
$L_{2b}$ is a linker between the second solubilization tag and the intein sequence
in $P_{2n}$, $P_2$ is a second purification tag with "n" occurrences, where n is an integer ranging from 1-6; and
$L_{2a}$ is a linker between the second solubilization tag and the second purification tag;

wherein $P_1$ is different from $P_2$;
wherein $P_{1n}$, $L_{1a}$, $S_1$, $L_{1b}$, $D_1$, and $L_1$ together form a first purification domain; and
wherein $L_2$, $D_2$, $L_{2b}$, $S_2$, $L_{2a}$, and $P_{2n}$ together form a second purification domain.

2. The fusion protein of claim 1, wherein n is 2, 3 or 4.

3. The fusion protein of claim 2, wherein n is 2.

4. The fusion protein of claim 1, wherein the $P_1$ and $P_2$ purification tags are affinity tags selected from the group consisting of polyhistidine (His-tag), FLAG tag, haemagglutinin (HA), MYC, streptavidin (Strep-tag), calmodulin binding peptide (CBP), and the intein-chitin binding domain (intein-CBD); wherein when the purification tag is a His-tag, the His-tag is n; wherein n is an integer ranging from 1-6.

5. The fusion protein is claim 4, wherein $P_1$ is the His-tag, $H_6$ and $P_2$ is the Strep-tag, Strep II.

6. The fusion protein of claim 5, comprising at least two His-tags and at least two Strep-tags.

7. The fusion protein of claim 5, $L_1$ and $L_2$ are absent.

8. The fusion protein of claim 1, wherein:
(a) the solubilization tags $S_1$ and $S_2$ are selected from the group consisting of thioredoxin (TRX), poly (NANP), MBP (maltose binding protein), and GST (glutathione-s-transferase);
(b) $D_2$ comprises residues 235-432 of SEQ ID NO: 1 or Mth RIR1; and
(c) the linker is selected from the group consisting of GGGGS (SEQ ID NO:5), GGGS (SEQ ID NO:6), GGSS (SEQ ID NO:7), Thr-Gly-Leu-Thr-Gly-Leu-Asn-Ser-Gly-Leu (SEQ ID NO: 8), GSE (SEQ ID NO:9), Gly-Ser, Gly-Ser-Gly-Ser (SEQ ID NO:10), Ala-Ser, $(Gly_4\text{-Ser})_3$ (SEQ ID NO:11), and $(Gly_4\text{-Ser})_4$ (SEQ ID NO:12), GSGSGSGS (SEQ ID NO:13) and SGSG (SEQ ID NO:15).

9. The fusion protein of claim 7, wherein when $P_1$ is H6, the linker is GGSS (SEQ ID NO:7), $P_2$ is a strep tag, and the linker is GGGSGGGSGGS (SEQ ID NO: 21).

10. The fusion protein of claim 1, wherein Ls comprises the amino acid sequence GSE; in $P_{1n}$, $P_1$ is $H_6$ and n is 2; $L_{1a}$ comprises GGSS (SEQ ID NO:7); $S_1$ is TRX; $L_{1b}$ comprises GGSS (SEQ ID NO:7); $D_1$ is SUMO; L1 is present or optional; L2 is present or optional; $D_2$ is intein; $L_{2b}$ comprises the amino acid sequence TGLTGLNSGL (SEQ ID NO: 8); $S_2$ is TRX; and $L_{2a}$ comprises GGSS (SEQ ID NO:7); and in $P_{2n}$, $P_2$ is a Strep-tag and n is 2.

11. A fusion protein comprising a target protein and the amino acid sequence of SEQ ID: NO:1.

12. The fusion protein of claim 1, wherein Ls, $L_1a$; $L_{1b}$, $L_1$, $L_2$, $L_{2b}$ and $L_{2a}$ are present.

13. The fusion protein of claim 1, wherein Ls, $L_1a$; $L_{1b}$, $L_1$, $L_2$, $L_{2b}$ and $L_{2a}$ independently comprise between two and twenty amino acids.

\* \* \* \* \*

SEQUENCE LISTING

```
<160> NUMBER OF SEQ ID NOS: 26

<210> SEQ ID NO 1
<211> LENGTH: 583
<212> TYPE: PRT
<213> ORGANISM: Artificial sequencew
<220> FEATURE:
<223> OTHER INFORMATION: Synthetic peptide

<400> SEQUENCE: 1

Met Gly Ser Gln His His His His His His Gly Gly Ser Ser His His
1               5                   10                  15

His His His His Gly Gly Ser Ser Ser Asp Lys Ile Ile His Leu Thr
                20                  25                  30

Asp Asp Ser Phe Asp Thr Asp Val Leu Lys Ala Asp Gly Ala Ile Leu
                35                  40                  45

Val Asp Phe Trp Ala Glu Trp Cys Gly Pro Cys Lys Met Ile Ala Pro
    50                  55                  60

Ile Leu Asp Glu Ile Ala Asp Glu Tyr Gln Gly Lys Leu Thr Val Ala
65                  70                  75                  80

Lys Leu Asn Ile Asp Gln Asn Pro Gly Thr Ala Pro Lys Tyr Gly Ile
                85                  90                  95

Arg Gly Ile Pro Thr Leu Leu Leu Phe Lys Asn Gly Glu Val Ala Ala
                100                 105                 110
```

```
Thr Lys Val Gly Ala Leu Ser Lys Gly Gln Leu Lys Glu Phe Leu Asp
            115                 120                 125

Ala Asn Leu Ala Gly Gly Ser Ser Leu Gln Asp Ser Glu Val Asn Gln
        130                 135                 140

Glu Ala Lys Pro Glu Val Lys Pro Glu Val Lys Pro Glu Thr His Ile
145                 150                 155                 160

Asn Leu Lys Val Ser Asp Gly Ser Ser Glu Ile Phe Phe Lys Ile Lys
                165                 170                 175

Lys Thr Thr Pro Leu Arg Arg Leu Met Glu Ala Phe Ala Lys Arg Gln
            180                 185                 190

Gly Lys Glu Met Asp Ser Leu Arg Phe Leu Tyr Asp Gly Ile Arg Ile
        195                 200                 205

Gln Ala Asp Gln Ala Pro Glu Asp Leu Asp Met Glu Asp Asn Asp Ile
    210                 215                 220

Ile Glu Ala His Arg Glu Gln Ile Gly Gly Cys Ile Thr Gly Asp Ala
225                 230                 235                 240

Leu Val Ala Leu Pro Glu Gly Glu Ser Val Arg Ile Ala Asp Ile Val
                245                 250                 255

Pro Gly Ala Arg Pro Asn Ser Asp Asn Ala Ile Asp Leu Lys Val Leu
            260                 265                 270

Asp Arg His Gly Asp Pro Val Leu Ala Asp Arg Leu Phe His Ser Gly
        275                 280                 285

Glu His Pro Val Tyr Thr Val Arg Thr Val Glu Gly Leu Arg Val Thr
    290                 295                 300

Gly Thr Ala Asn His Pro Leu Leu Cys Leu Val Asp Val Ala Gly Val
305                 310                 315                 320

Pro Thr Leu Leu Trp Lys Leu Ile Asp Glu Ile Lys Pro Gly Asp Phe
                325                 330                 335

Ala Val Ile Gln Arg Ser Ala Phe Ser Val Asp Cys Ala Gly Phe Ala
            340                 345                 350

Arg Gly Lys Pro Glu Phe Ala Pro Thr Thr Tyr Thr Val Gly Val Pro
        355                 360                 365

Gly Leu Val Arg Phe Leu Glu Ala His His Arg Asp Pro Asp Ala Gln
    370                 375                 380

Ala Ile Ala Asp Glu Leu Thr Asp Gly Arg Phe Tyr Tyr Ala Lys Val
385                 390                 395                 400

Ala Ser Val Thr Asp Ala Gly Val Gln Pro Val Tyr Ser Leu Arg Val
                405                 410                 415

Asp Thr Ala Gln Asp His Ala Phe Thr Asn Gly Phe Val Ser His Ala
            420                 425                 430

Thr Gly Leu Thr Gly Leu Asn Ser Gly Leu Ser Asp Lys Ile Ile His
        435                 440                 445

Leu Thr Asp Asp Ser Phe Asp Thr Asp Val Leu Lys Ala Asp Gly Ala
    450                 455                 460

Ile Leu Val Asp Phe Trp Ala Glu Trp Cys Gly Pro Cys Lys Met Ile
465                 470                 475                 480

Ala Pro Ile Leu Asp Glu Ile Ala Asp Glu Tyr Gln Gly Lys Leu Thr
                485                 490                 495

Val Ala Lys Leu Asn Ile Asp Gln Asn Pro Gly Thr Ala Pro Lys Tyr
            500                 505                 510

Gly Ile Arg Gly Ile Pro Thr Leu Leu Leu Phe Lys Asn Gly Glu Val
        515                 520                 525

Ala Thr Lys Val Gly Ala Leu Ser Lys Gly Gln Leu Lys Glu Phe Leu
```

Asp Ala Asn Leu Ala Gly Ser Ser Ala Trp Ser His Pro Gln Phe Glu
545                 550                 555                 560

Phe Glu Lys Gly Gly Gly Ser Gly Gly Gly Ser Gly Gly Ser Ala Trp
                565                 570                 575

Ser His Pro Gln Phe Glu Lys
            580

<210> SEQ ID NO 2
<211> LENGTH: 1020
<212> TYPE: DNA
<213> ORGANISM: Artificial Sequence
<220> FEATURE:
<223> OTHER INFORMATION: Synthetic nucleotide encoding TSGIT

<400> SEQUENCE: 2
atgggcagcc aacatcacca tcaccatcac cgtggtggca gctctcatca ccatcatcat    60
cacggtggct ctagcagcga taaaattatt cacctgactg acgacagttt tgacacggat   120
gtactcaaag cggacggggc gccgaaatat ggcatccgtg gtatcccgac tctgctgctg   180
ttcaaaaacg gtgaagtggc ggaaccaaag tgggtgcact gtctaaaggt cagttgaaag   240
agttcctcga cgctaacctg gccggcggta gctctctgca ggactcagaa gtcaatcaag   300
aagctaagcc agaggtcaag ccagaagtca agcctgagac tcacatcaat ttaaaggtgt   360
ccgatggatc ttcagagatc ttcttcaaga tcaaaaagac cactccttta agaaggctga   420
tggaagcgtt cgctaaaaga cagggtaagg aaatggactc cttaagattc ttgtacgacg   480
gtattagaat tcaagctgat caggcccctg aagatttgga catggaggat aacgatatta   540
ttgaggctca ccgccaacag attcgaggtt gcatcacggg agatgcacta gttgccctac   600
ccgagggcga gtcggtacgc atcgccgaca tcgtgccggg tgcgcggccc aacagtgaca   660
acgccatcga cctgaaagtc cttgaccggc atggcaatcc cgtgctcgcc ccgattctgg   720
atgaaatcgc tgacgaatat caggggcaaac tgaccgttgc aaaactgaac atcgatcaaa   780
accctgcgcc gaaatatggc atccgtggta tcccgactct gctgctgttc aaaaaccgtg   840
aaggtgaagt ggcgaccaaa gtgggtctgt ctaaaggtca gttgaaagag ttcctcgacg   900
ctaacctggc cggtggcagc agctctgcat ggagccaccc accacaattt gagaagggag   960
gcggttctcg ttctggcgga agtggtggct ctgcatggtc caccctcaa ttcgagaagt    1020

<210> SEQ ID NO 3
<211> LENGTH: 236
<212> TYPE: PRT
<213> ORGANISM: Artificial Sequence
<220> FEATURE:
<223> OTHER INFORMATION: synthetic peptide

<400> SEQUENCE: 3

Val Ser Lys Gly Glu Glu Leu Ile Lys Glu Asn Met Arg Met Lys Val
1               5                   10                  15

Val Met Glu Gly Ser Val Asn Gly His Gln Phe Lys Cys Thr Gly Glu
            20                  25                  30

Gly Glu Gly Arg Pro Tyr Glu Gly Val Gln Thr Met Arg Ile Lys Val
        35                  40                  45

Ile Glu Gly Gly Pro Leu Pro Phe Ala Phe Asp Ile Leu Ala Thr Ser
    50                  55                  60

Phe Met Tyr Gly Ser Arg Thr Phe Ile Lys Tyr Pro Ala Asp Ile Pro
65                  70                  75                  80

Asp Phe Phe Lys Gln Ser Pro Glu Gly Phe Thr Trp Glu Arg Val
            85                  90                  95

Thr Arg Tyr Glu Asp Gly Gly Val Val Thr Val Thr Gln Asp Thr Ser
            100                 105                 110

Leu Glu Asp Gly Glu Leu Val Tyr Asn Val Lys Val Arg Gly Val Asn
            115                 120                 125

Phe Pro Ser Asn Gly Pro Val Met Gln Lys Lys Thr Lys Gly Trp Glu
130                 135                 140

Pro Asn Thr Glu Met Met Tyr Pro Ala Asp Gly Gly Leu Arg Gly Tyr
145                 150                 155                 160

Thr Asp Ile Ala Leu Lys Val Asp Gly Gly His Leu His Cys Asn
            165                 170                 175

Phe Val Thr Thr Tyr Arg Ser Lys Lys Thr Val Gly Asn Ile Lys Met
            180                 185                 190

Pro Gly Val His Ala Val Asp His Arg Leu Glu Arg Ile Glu Glu Ser
            195                 200                 205

Asp Asn Glu Thr Tyr Val Val Gln Arg Glu Val Ala Val Ala Lys Tyr
        210                 215                 220

Ser Asn Leu Gly Gly Gly Met Asp Glu Leu Tyr Lys
225                 230                 235

<210> SEQ ID NO 4
<211> LENGTH: 708
<212> TYPE: DNA
<213> ORGANISM: Artificial Sequence
<220> FEATURE:
<223> OTHER INFORMATION: Synthetic nucleotide encoding mRuby3

<400> SEQUENCE: 4
gtaagtaaag gggaggagct tatcaaagaa aatatgcgca tgaaggtggt catggaaggg      60
tcagtgaacg gtcaccagtt caaatgtacc ggtgaaggcg aaggccgtcc gtacgaaggc     120
gtacagacca tgcgcattaa agttattgag gaggaccgt tacccttcgc atttgacatc     180
cttgccacat ccttcatgta cggttcacgc accttcatta gtatccggc ggacattcca     240
gacttttca acaatctttt cccgaaggc tttacctggg agcgcgttac tcgctacgaa      300
gacggcgggg ttgttactgt gacgcaggac acttctttgg aagacggtga attagtttac      360
aacgtaaaag tgcgtggcgt gaacttccca gtaacggtc cggtgatgca aaagaagacc     420
aagggatggg aaccaaatac ggagatgatg tacccggcag acggcggact gcgtggatat     480
acggacatcg cattaaaggt tgacggcggg gggcacttac attgcaattt tgtaactacg     540
taccgttcga agaagacggt tggaaacatc aagatgcccg gagtccacgc tgtggaccat     600
cgccttgagc gcatcgagga gtcagataac gaaacctatg ttgttcaacg tgaggtagct     660
gttgcaaaat acagcaatct gggggggggt atcgatgagt tgtataag             708

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide

<400> SEQUENCE: 5

Gly Gly Gly Gly Ser
1               5

```
<210> SEQ ID NO 6
<211> LENGTH: 4
<212> TYPE: PRT
<213> ORGANISM: Artificial Sequence
<220> FEATURE:
<223> OTHER INFORMATION: Synthetic peptide

<400> SEQUENCE: 6

Gly Gly Gly Ser
1

<210> SEQ ID NO 7
<211> LENGTH: 4
<212> TYPE: PRT
<213> ORGANISM: Artificial Sequence
<220> FEATURE:
<223> OTHER INFORMATION: Synthetic peptide

<400> SEQUENCE: 7

Gly Gly Ser Ser
1

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Thr Gly Leu Thr Leu Asn Ser Gly Leu
1               5

<210> SEQ ID NO 9
<211> LENGTH: 3
<212> TYPE: PRT
<213> ORGANISM: Artificial Sequence
<220> FEATURE:
<223> OTHER INFORMATION: Synthetic peptide

<400> SEQUENCE: 9

Gly Ser Glu
1

<210> SEQ ID NO 10
<211> LENGTH: 4
<212> TYPE: PRT
<213> ORGANISM: Artificial Sequence
<220> FEATURE:
<223> OTHER INFORMATION: Synthetic peptide

<400> SEQUENCE: 10

Gly Ser Gly Ser
1

<210> SEQ ID NO 11
<211> LENGTH: 15
<212> TYPE: PRT
<213> ORGANISM: Artificial Sequence
<220> FEATURE:
<223> OTHER INFORMATION: Synthetic peptide

<400> SEQUENCE: 11

Gly Gly Gly Gly Ser Gly Gly Gly Ser Gly Gly Gly Gly Ser
1               5                   10                  15

<210> SEQ ID NO 12
```

```
<211> LENGTH: 20
<212> TYPE: PRT
<213> ORGANISM: Artificial Sequence
<220> FEATURE:
<223> OTHER INFORMATION: Synthetic peptide

<400> SEQUENCE: 12

Gly Gly Gly Gly Ser Gly Gly Gly Ser Gly Gly Gly Ser Gly
1               5                   10                  15

Gly Gly Gly Ser
            20

<210> SEQ ID NO 13
<211> LENGTH: 8
<212> TYPE: PRT
<213> ORGANISM: Artificial Sequence
<220> FEATURE:
<223> OTHER INFORMATION: Synthetic peptide

<400> SEQUENCE: 13

Gly Ser Gly Ser Gly Ser Gly Ser
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(5)
<223> OTHER INFORMATION: n repeats

<400> SEQUENCE: 14

Gly Gly Gly Gly Ser
1               5

<210> SEQ ID NO 15
<211> LENGTH: 4
<212> TYPE: PRT
<213> ORGANISM: Artificial Sequence
<220> FEATURE:
<223> OTHER INFORMATION: Synthetic peptide

<400> SEQUENCE: 15

Ser Gly Ser Gly
1

<210> SEQ ID NO 16
<211> LENGTH: 8
<212> TYPE: PRT
<213> ORGANISM: Artificial Sequence
<220> FEATURE:
<223> OTHER INFORMATION: Synthetic peptide

<400> SEQUENCE: 16

Asp Tyr Lys Asp Asp Asp Asp Lys
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic peptide

<400> SEQUENCE: 17
```

<210> SEQ ID NO 18
<211> LENGTH: 10
<212> TYPE: PRT
<213> ORGANISM: Artificial Sequence
<220> FEATURE:
<223> OTHER INFORMATION: Synthetic peptide

<400> SEQUENCE: 18

Ile Leu Lys Lys Ala Thr Ala Tyr Ile Leu
1               5                   10

<210> SEQ ID NO 19
<211> LENGTH: 8
<212> TYPE: PRT
<213> ORGANISM: Artificial Sequence
<220> FEATURE:
<223> OTHER INFORMATION: Synthetic peptide

<400> SEQUENCE: 19

Trp Ser His Pro Gln Phe Glu Lys
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic peptide

<400> SEQUENCE: 20

Glu Gln Lys Leu Ile Ser Glu Glu Asp Leu
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic peptide

<400> SEQUENCE: 21

Gly Gly Gly Ser Gly Gly Gly Ser Gly Gly Ser
1               5                   10

<210> SEQ ID NO 22
<211> LENGTH: 231
<212> TYPE: PRT
<213> ORGANISM: Artificial sequence
<220> FEATURE:
<223> OTHER INFORMATION: Synthetic gp2.5

<400> SEQUENCE: 22

Ala Lys Lys Ile Phe Thr Ser Ala Leu Gly Thr Ala Glu Pro Tyr Ala
1               5                   10                  15

Tyr Ile Ala Lys Pro Asp Tyr Gly Asn Glu Glu Arg Gly Phe Gly Asn
                20                  25                  30

Pro Arg Gly Val Tyr Lys Val Asp Leu Thr Ile Pro Asn Lys Asp Pro
            35                  40                  45

Arg Cys Gln Arg Met Val Asp Glu Ile Val Lys Cys His Glu Glu Ala
        50                  55                  60

Tyr Ala Ala Ala Val Glu Glu Tyr Glu Ala Asn Pro Pro Ala Val Ala

```
                65                  70                  75                  80
Arg Gly Lys Lys Pro Leu Lys Pro Tyr Glu Gly Asp Met Pro Phe Phe
                    85                  90                  95

Asp Asn Gly Asp Gly Thr Thr Thr Phe Lys Phe Lys Cys Tyr Ala Ser
                100                 105                 110

Phe Gln Asp Lys Lys Thr Lys Glu Thr Lys His Ile Asn Leu Val Val
                115                 120                 125

Val Asp Ser Lys Gly Lys Met Glu Asp Val Pro Ile Ile Gly Gly
        130                 135                 140

Gly Ser Lys Leu Lys Val Lys Tyr Ser Leu Val Pro Tyr Lys Trp Asn
145                 150                 155                 160

Thr Ala Val Gly Ala Ser Val Lys Leu Gln Leu Glu Ser Val Met Leu
                165                 170                 175

Val Glu Leu Ala Thr Phe Gly Gly Glu Asp Asp Trp Ala Asp Glu
                180                 185                 190

Val Glu Glu Asn Gly Tyr Val Ala Ser Gly Ser Ala Lys Ala Ser Lys
                195                 200                 205

Pro Arg Asp Glu Glu Ser Trp Asp Glu Asp Glu Glu Ser Glu Glu
        210                 215                 220

Ala Asp Glu Asp Gly Asp Phe
225                 230
```

```
<210> SEQ ID NO 23
<211> LENGTH: 693
<212> TYPE: DNA
<213> ORGANISM: Artificial sequence
<220> FEATURE:
<223> OTHER INFORMATION: Synhetic nucleotide enclloding gp2.5

<400> SEQUENCE: 23
gctaagaaga ttttcacctc tgcgctgggt accgctgaac cttacgctta catcgccaag    60
cdggactacg gcaacgaaga gcgtggcttt gggaacccct cgtggtgtcta taaagttgac   120 ctgactattc ccaacaaaga cccgcgctgc cagcgtatgg tcgatgaaat cgtgaagtgt   180
cacgaagagg cttatgctgc tgccgttgag gaatacgaag ctaatccacc tgctgtagct   240
cgtcgtaaga aaccgctgaa acccctatgag cgtcacatcc cgttcttcga taacggtgac   300
ggtacgacta ccttttaagtt caaatgctac gcgtcttctc aagacaagaa gaagaaagag   360
accaagcaca tcaatctggt tgtggttgac tcaaaaggta agaagatgga agacgttccg   420
attatcggtg gtggctctaa gctgaaagtt aaatattctc tggttccata caagtggaac   480
actgctgtag gtgcgagcgt taagctgcaa ctggaatccg tgatgctggt cgaactggct   540
acctttggtg gcggtgaaga cgattgggct gacgaagttg aagagaacgg ctatgttgcc   600
tctggttctg ccaaagcgag caaaccacgc gacgaagaaa gctgggacga agacgacgaa   660
gagtccgagg aagcagacga agacggagac ttc                                693
```

```
<210> SEQ ID NO 24
<211> LENGTH: 29
<212> TYPE: PRT
<213> ORGANISM: Artificial Sequence
<220> FEATURE:
<223> OTHER INFORMATION: Synthetic peptide

<400> SEQUENCE: 24

Ala Trp Ser His Pro Gln Phe Glu Lys Gly Gly Gly Ser Gly Gly Gly
1               5                   10                  15
```

Ser Gly Gly Ser Ala Trp Ser His Pro Gln Phe Glu Lys
               20                  25

<210> SEQ ID NO 25
<211> LENGTH: 62
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: Digoxigenin modiified
<220> FEATURE:
<221> NAME/KEY: misc_feature
<222> LOCATION: (39)..(40)
<223> OTHER INFORMATION: linked by Biotin

<400> SEQUENCE: 25
ctagaggatc cccgggtacc gagctcgaat tcgtaatcat ggtcatagct gtttcctgtg    60
tg                                                                  62

<210> SEQ ID NO 26
<211> LENGTH: 20
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<222> LOCATION: (16)..(17)
<223> OTHER INFORMATION: iCy3

<400> SEQUENCE: 26
tgaatgaatg actgccgact                                               20